United States Patent
Stefanov

(10) Patent No.: US 10,456,521 B2
(45) Date of Patent: Oct. 29, 2019

(54) MEDICAMENT DELIVERY DEVICE WITH A CONTROL MECHANISM

(71) Applicant: CAREBAY EUROPE LTD, Sliema (MT)

(72) Inventor: Slobodan Stefanov, Deerfield Beach, FL (US)

(73) Assignee: SHL MEDICAL AG, Zug (CH)

( * ) Notice: Subject to any disclaimer, the term of this patent is extended or adjusted under 35 U.S.C. 154(b) by 360 days.

(21) Appl. No.: 15/523,588

(22) PCT Filed: Oct. 2, 2015

(86) PCT No.: PCT/EP2015/072815
§ 371 (c)(1),
(2) Date: May 1, 2017

(87) PCT Pub. No.: WO2016/074850
PCT Pub. Date: May 19, 2016

(65) Prior Publication Data
US 2017/0296742 A1    Oct. 19, 2017

(30) Foreign Application Priority Data

Nov. 10, 2014  (SE) ...................................... 1451347

(51) Int. Cl.
*A61M 5/142*    (2006.01)
*A61M 5/145*    (2006.01)
(Continued)

(52) U.S. Cl.
CPC ...... *A61M 5/14248* (2013.01); *A61M 5/1452* (2013.01); *A61M 5/142* (2013.01);
(Continued)

(58) Field of Classification Search
CPC .......... A61M 5/14248; A61M 5/14244; A61M 2005/14252; A61M 2005/14256;
(Continued)

(56) References Cited

U.S. PATENT DOCUMENTS

2005/0197650 A1    9/2005  Sugimoto et al.
2005/0261693 A1   11/2005  Miller et al.
(Continued)

FOREIGN PATENT DOCUMENTS

CN    1663626 A     9/2005
EP    1326659 B1   12/2005
(Continued)

OTHER PUBLICATIONS

International Search Report and Written Opinion for Int. App. No. PCT/EP2015/072815, completed Dec. 4, 2015.

*Primary Examiner* — Kevin C Sirmons
*Assistant Examiner* — Leah J Swanson
(74) *Attorney, Agent, or Firm* — McDonnell Boehnen Hulbert & Berghoff LLP

(57) ABSTRACT

A control mechanism for a medicament delivery device is provided having a medicament container connection mechanism, for connecting a medicament container with a medicament delivery member; a penetration and withdrawal mechanism, for actuating a penetration and a withdrawal sequence; a medicament delivery drive unit, for expelling a medicament; an activation mechanism, for initiating a penetration and medicament delivery sequence; a stop mechanism, for initiating a withdrawal sequence; wherein the control mechanism further comprises a control member, linearly movable between a first position and a second position, which control member is connectable to the medicament container connection mechanism, to the penetration and withdrawal mechanism, to the medicament delivery drive unit, to the activation mechanism, and to the stop mechanism.

18 Claims, 18 Drawing Sheets

(51) Int. Cl.
*A61M 5/20* (2006.01)
*A61M 5/32* (2006.01)

(52) U.S. Cl.
CPC .............. *A61M 5/20* (2013.01); *A61M 5/3257* (2013.01); *A61M 2005/14256* (2013.01); *A61M 2005/206* (2013.01)

(58) Field of Classification Search
CPC ........ A61M 2005/1426; A61M 5/1452; A61M 5/142; A61M 5/145; A61M 5/1454; A61M 2005/14506; A61M 2005/14533
See application file for complete search history.

(56) References Cited

U.S. PATENT DOCUMENTS

| | | |
|---|---|---|
| 2006/0095014 A1 | 5/2006 | Ethelfeld |
| 2007/0167920 A1 | 7/2007 | Hommann |
| 2012/0022499 A1 | 1/2012 | Anderson et al. |

FOREIGN PATENT DOCUMENTS

| | | |
|---|---|---|
| TW | 201443 | 1/1993 |
| WO | 2010/112377 A1 | 10/2010 |
| WO | 2013/078200 A1 | 5/2013 |
| WO | 2013/153041 A2 | 10/2013 |
| WO | 2013/155153 A1 | 10/2013 |

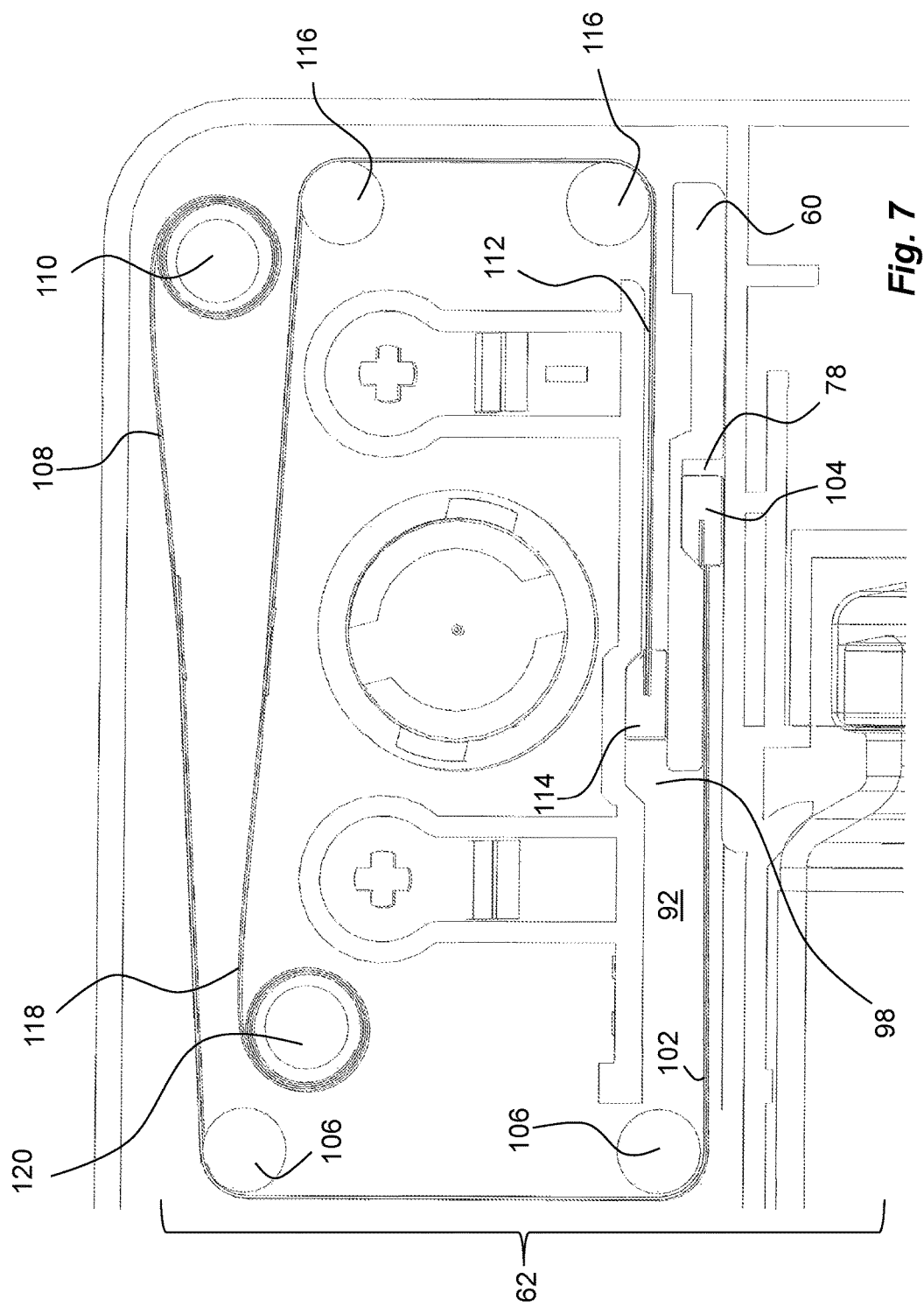

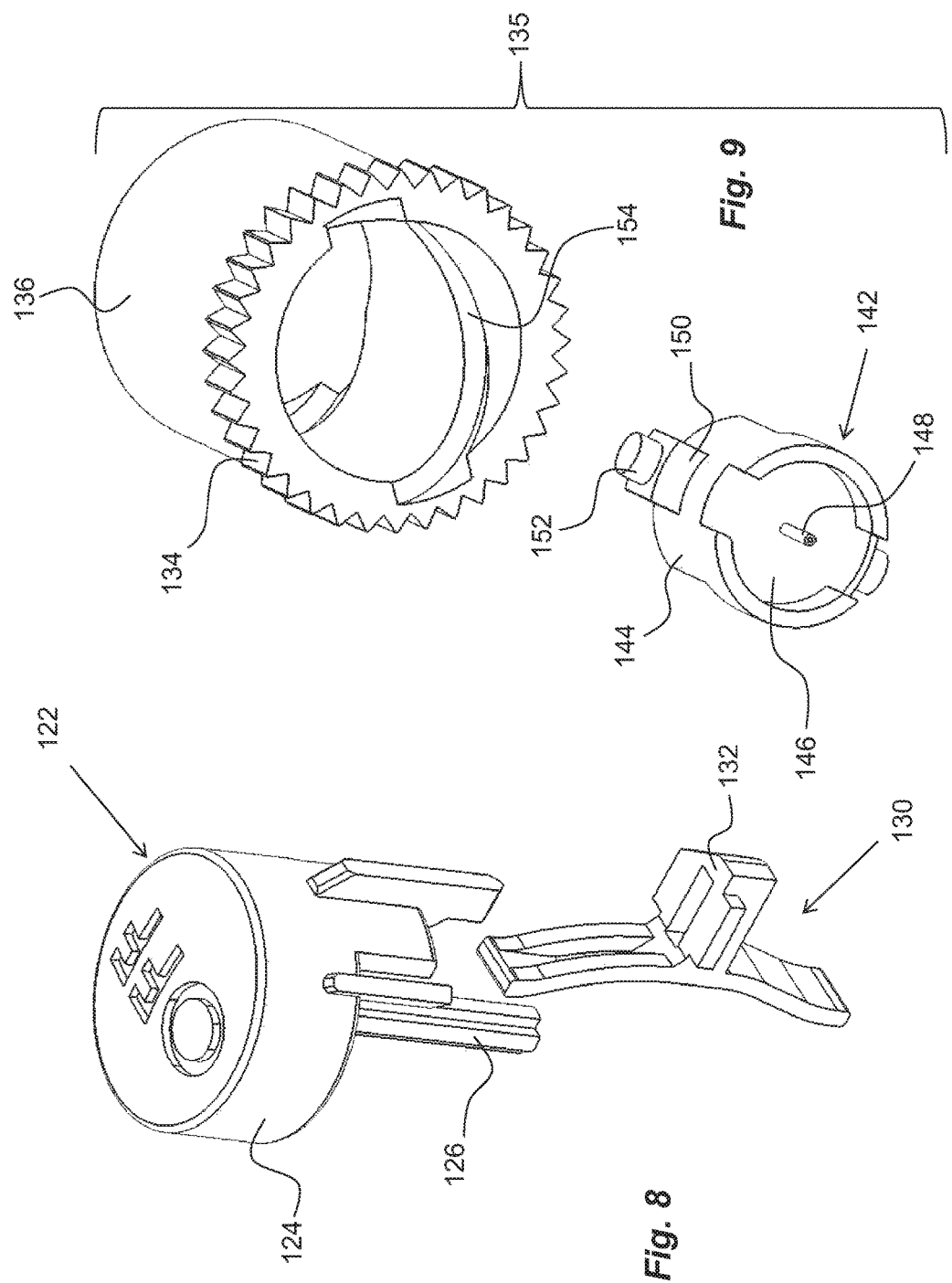

MEDICAMENT DELIVERY DEVICE WITH A CONTROL MECHANISM

CROSS REFERENCE TO RELATED APPLICATIONS

The present application is a U.S. National Phase Application pursuant to 35 U.S.C. § 371 of International Application No. PCT/EP2015/072815 filed Oct. 2, 2015, which claims priority to Swedish Patent Application No. 1451347-7 filed Nov. 10, 2014. The entire disclosure contents of these applications are herewith incorporated by reference into the present application.

TECHNICAL AREA

The present disclosure relates to a control mechanism for a medicament delivery device and in particular to a device of limited size, capable of accurately controlling a number of functions of a medicament delivery device.

BACKGROUND

For a number of years, infusers have been used that provide the patient or user with the means for administering a drug in an easy way without requiring a medically trained person, such as a physician or a nurse, to handle the device.

In order to reduce the size of the infuser, a number of alternative designs regarding the plunger rod have been developed, in particular since the plunger rod conventionally is an elongated rod having a length that enables it to empty a tubular medicament container. Document EP 1 326 659 discloses an injecting device having a flexible plunger rod bendable around a guiding wheel. The plunger rod is driven by an electric motor, via a transmission, to empty a medicament container. The drawback with the solution according to EP 1 326 659 is that the guiding wheel is rather large and is positioned behind the medicament container, as seen in a longitudinal direction, making the device unnecessary long.

Document WO 2010/112377 discloses a reusable medicament delivery device. In order to reduce the length of the device, the plunger rod is arranged in two telescopically arranged parts. The telescopic action requires two compression springs, rendering the device rather long. The device is further arranged with an electric motor. The motor, operably connected to an elongate member, is arranged to control the dose delivery movement of the plunger rods. Further, the motor is also used for retracting the plunger rods after completed dose delivery in order to be able to replace the medicament container.

Another drawback with many of the mentioned devices is that there is no feature or mechanism for handling the injection needle after completed injection. When the device is withdrawn, the injection needle is completely exposed and may cause injuries to persons handling the device after use.

SUMMARY

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is/are located closest to the medicament delivery site of the patient.

The aim of the present disclosure is to provide a control mechanism having a number of automatic features and wherein the number of components is kept as low as possible.

The control mechanism according to the present application is adapted for a medicament delivery device, which medicament delivery device preferably comprises a medicament container connection mechanism, for connecting a medicament container with a medicament delivery member; a penetration and withdrawal mechanism, for actuating a penetration and a withdrawal sequence; a medicament delivery drive unit, for expelling a medicament; an activation mechanism, for initiating a penetration and medicament delivery sequence; a stop mechanism, for initiating a withdrawal sequence; wherein said control mechanism further comprises a control member, linearly movable between a first position and a second position, which control member is directly connectable to the medicament container connection mechanism, to the penetration and withdrawal mechanism, to the medicament delivery drive unit, to the activation mechanism, and to the stop mechanism, such that the different functions are actuated by the single control member.

According to a further aspect, the control member is directly connected to the activation mechanism when the control member is in the first position, and the control member is directly connected to the penetration and withdrawal mechanism and to the medicament container connection mechanism during linear movement of the control member between the first and the second position, and the control member is also directly connected to the medicament delivery drive unit and to the stop mechanism when the control member is in the second position. The control member is manually actuatable when it is in the first position or in the second position.

According to a another aspect, the activation mechanism comprises a manually actuated first locking element and wherein the control member comprises a first recess in which said first locking element is accommodated, such that the control member is directly connected to the activation mechanism when the control member is in the first position. The first locking element is connected to a push button of the activation mechanism, which push button may be pressed by a user to actuate the control mechanism.

According to yet a further aspect, the control member is releasably held in the first position by said first locking element against a bias of a pre-tensioned first force element, and wherein manual actuation of the first locking element releases the control member to move linearly from the first position towards the second position under the bias of the first force element.

According to yet another aspect, the first force element comprises a first anchoring element and the control member comprises a first seat and wherein the first anchoring element is releasably connected to the first seat, and configured to be disconnected from the first seat when the control member arrives at the second position.

According to a another aspect, the medicament delivery drive unit comprises an electrical circuit having a second lead and a third lead and wherein the control member comprises a conductive surface to which said second lead and said third lead are directly connected when the control member is in the second position such that said electrical circuit is closed.

According to a further aspect, the stop mechanism comprises a manually actuated second locking element and wherein the control member comprises a second recess in which said second locking element may be accommodated, and configured such that the control member is directly connected to the stop mechanism when the control member arrives at the second position.

According to one aspect, the control member may further be releasably held in the second position by said second locking element against a bias of a pre-tensioned second force element, and wherein manual actuation of the second locking element releases the control member to move linearly from the first position towards the second position under the bias of the second force element. Accordingly, the control element is stationary in the second position, keeping the circuit closed, until the stop mechanism is actuated by a user pressing a push button of the stop mechanism.

According to yet an aspect, the second force element comprises a second anchoring element and the control member comprises a second seat and wherein the second anchoring element is configured to be connected to the second seat when the control member arrives at the second position.

According to a further aspect, the penetration and withdrawal mechanism comprises a pinion arranged on a rotatable sleeve, and the control member comprises a toothed rack, and wherein linear movement of the control member between the first position and the second position causes rotation of said rotatable sleeve via interaction between said pinion and said toothed rack. Since a delivery member, e.g. a needle, is threadedly connected to the rotatable sleeve, rotation of the sleeve causes a penetration or a withdrawal of the delivery member when the control member moves between the first position and the second position.

According to one further aspect, the medicament container connection mechanism comprises a movable body arranged with a ledge, and the control member comprises a slit, which slit has a stop surface, and wherein linear movement of the control member from the first position to the second position causes movement of the body via interaction between said ledge and said stop surface. Such a body may comprise a piercing needle that is moved to penetrate a septum of a medicament container. The piercing needle may also be connected to the delivery member via a flexible tube, such that piercing of the septum connects the drug of the medicament container with the delivery member.

In order to expel doses of medicament from the medicament container to the medicament delivery member, the drive unit may further comprise a plunger rod, which plunger rod may comprise a number of distinct separate segments being inter-connectable to each other for forming an elongated plunger rod. The use of distinct separate segments enables a very compact device because the elongated plunger rod is "built" by separate successive segments, one at a time. Since the segments are separate, the segments may be packed closely together. There is no need to make room for a plunger rod that is bent or arch-shaped. Thus, the length of a conventional elongated plunger rod does not dictate the size of the medicament delivery device in the present case.

In order to drive the plunger rod into the medicament container for expelling a dose of medicament, the plunger rod elements may be arranged with threads, designed to interact with a plunger rod drive wheel rotatably connected to an electric motor of the drive unit.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

FIG. 7 shows a different detailed view of components comprised in the medicament delivery device of FIG. 1.

FIG. 8 shows a different detailed view of components comprised in the medicament delivery device of FIG. 1.

FIG. 9 shows a different detailed view of components comprised in the medicament delivery device of FIG. 1.

DETAILED DESCRIPTION

Figure 1:
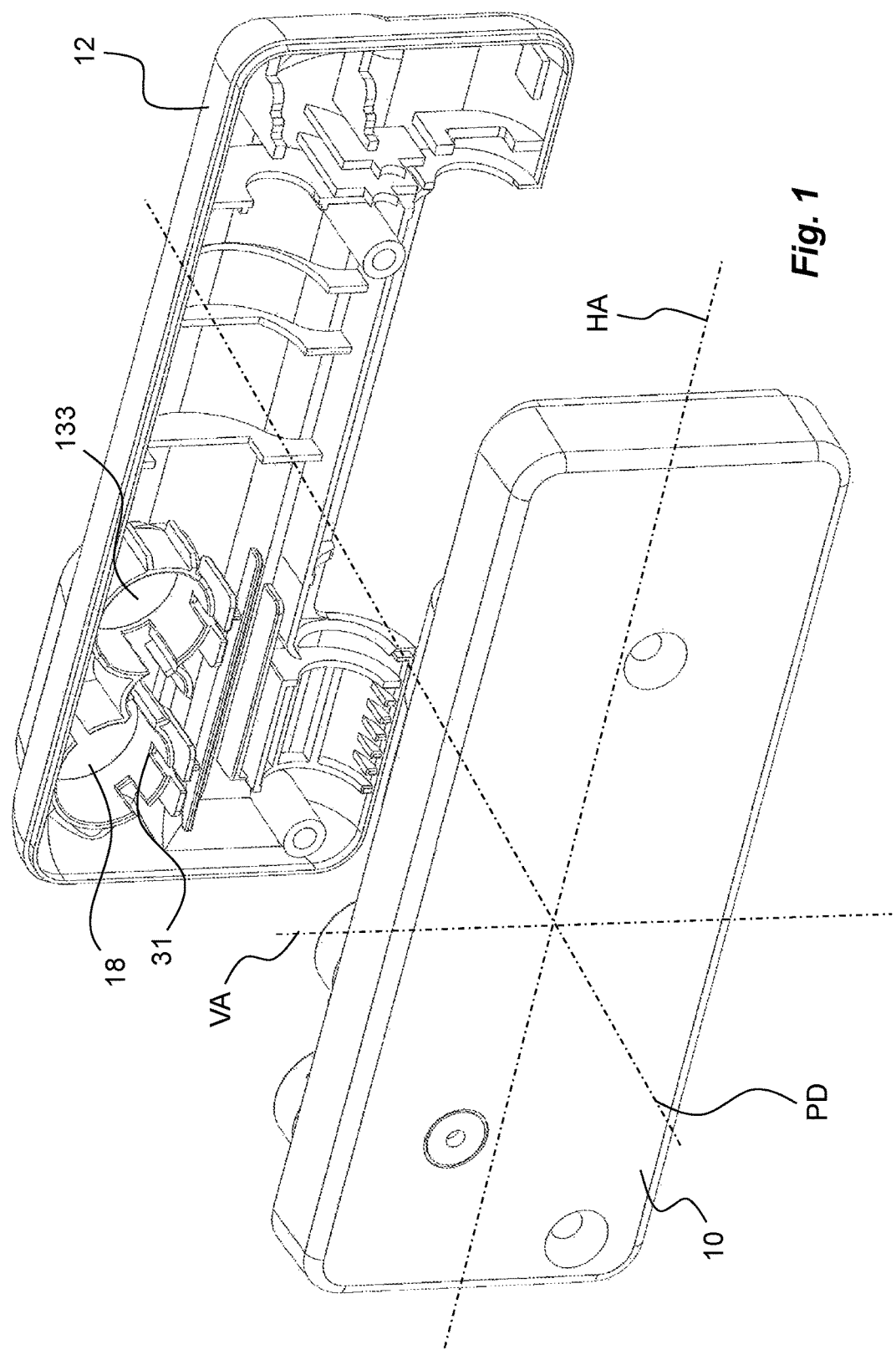
FIG. 1 is a perspective view of a medicament delivery device where one housing part is detached for clarity.

The exemplary embodiment shown in the drawings comprises a proximal housing part 10 and a distal housing part 12. It is however to be understood that the device can comprise further housing parts depending on design and production issues. The distal housing part 12 is arranged to accommodate a number of elements and mechanisms. Preferably, the assembled housing has a generally flat, rectangular shape having a measure or thickness, viewed along a proximal-distal axis, PD, that is much less than the dimensions in the other two directions, vertical axis VA and horizontal axis HA.

An activation mechanism 14 is arranged in the device for activating different functions of the device as will be described, see FIG. 2. The activation mechanism 14 comprises a push button 16, extending through a passage 18 of the distal housing part 12. The push button 16 comprises a generally tubular body 20 provided with an end wall 22, FIG. 4, which acts as contact surface for a user as will be described. The push button 16 may be arranged with indicia that provide the user with information regarding its function, such as the word ON, indicating to a user that this is the button that activates the device. A centrally positioned shaft 24 is arranged on the end wall, extending in the proximal direction. The shaft 24 is arranged to fit into a generally tubular guide post 26 in the proximal housing part 10, FIG. 5. The body 20 of the push button 16 is further arranged with two longitudinally extending ledges 28, FIG. 4*b*, arranged opposite each other. The ledges 28 are attached such that they extend a distance radially from the side surface of the tubular body 20. A distally directed stop surface 30 is thereby formed on each ledge 28, which stop surface 30 is in contact with an inner surface 31, FIG. 1, of the distal housing part 12 around the passage 18, when the push button 16 is forced in the distal direction as will be described.

Further a proximally directed stop surface 32 is formed by the opposite end of the ledge 28, which stop surface 32 is intended to come in contact with an inner surface of the proximal housing part 10 when the push button 16 is pressed, thereby limiting the movement of the push button 16. The body 20 of the push button 16 is further arranged with an extension 34 in the proximal direction. On the extension 34 an elongated ledge 36 is integrated, which ledge 36 extends on both sides of the extension 34 and the body 20. The side surface of the elongated ledge 36 facing radially inwards is arranged with an inclined surface 38, FIG. 4*a*.

Figure 4:
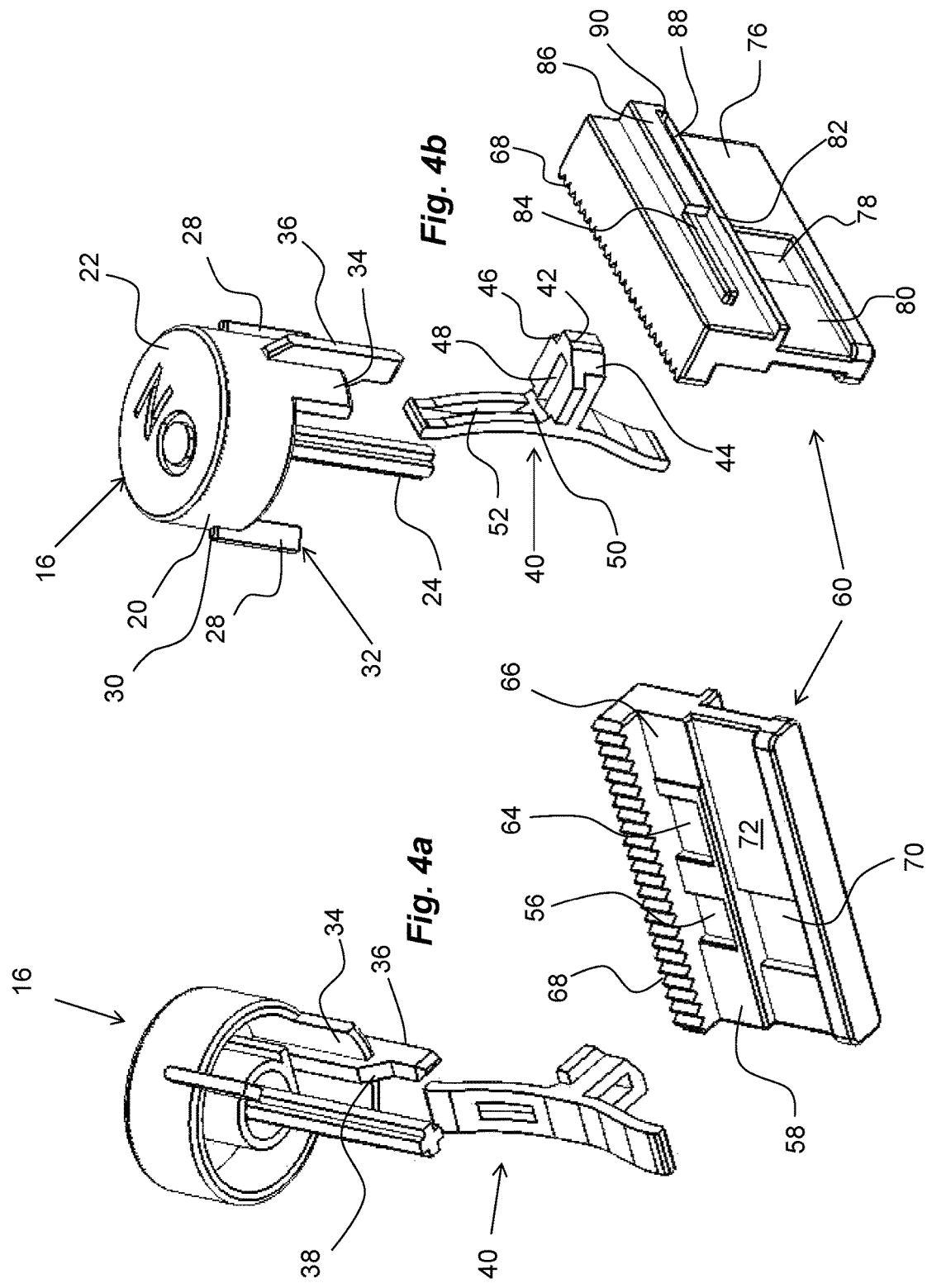
FIG. 4 shows a different detailed view of components comprised in the medicament delivery device of FIG. 1.

The activation mechanism further comprises a support element 40 in the form of an arc-shaped elongated plate, operably connected to the push button 16, FIG. 4, hereafter named wedge lock pin. Generally in the centre of the wedge lock pin, a protrusion 42 is arranged, forming a first locking element. The end surface of the protrusion 42 is arranged with a bevelled surface 44 at one corner and a cut-out 46 at the other corner. The protrusion 42 is further arranged with a central slit 48, through which the elongated ledge 36 fits such that the inclined surface 38 of the elongated ledge 36 is in contact with an inclined surface 50 arranged between the central slit 48 and a longitudinal slit 52 in the wedge lock pin 40, as seen in FIG. 4*b*. The wedge lock pin 40 is seated with a proximal end in a seat 54 in the proximal housing part, FIG. 6. The distal end of the wedge lock pin 40 extends into the interior of the body 20 of the push button 16.

The protrusion 42 of the wedge lock pin 40 is accommodated in a first seat 56 on a first side surface 58 of a generally plate-shaped control element 60, FIG. 4, comprised in a control mechanism 62. A second seat 64 is further arranged on the first side surface 58 of the control element, offset in relation to the first seat 56. Further, the first side surface 58 of the control element 60 is arranged with power connection elements in the form of a surface 66 of conductive material, the function of which will be described below. The first side surface 58 is further arranged with a toothed rack 68. Further the first side surface 58 is arranged with a third seat 70 positioned in a longitudinally extending groove 72, which groove 72 extends the whole width of the control element 60.

The opposite side surface, i.e. the second side surface 76, is also arranged with a first seat 78 as well as a groove 80. In this case the groove 80 extends only to one end of the control element 60. The second side surface 76 is further arranged with a longitudinally extending first ledge 82. A second longitudinally extending ledge 84 is positioned parallel with, and at a distance to, the first ledge 82. The second ledge 84 is further arranged with a third ledge 86 extending a certain length of the second ledge 84, where the third ledge 86 is positioned 90 degrees in relation to the second ledge 84. The third ledge 86 thereby extends towards the first ledge 82, creating an elongated slit 88 between the third ledge 86 and the first ledge 82. The slit 88 ends in a stop surface 90.

Figure 5:
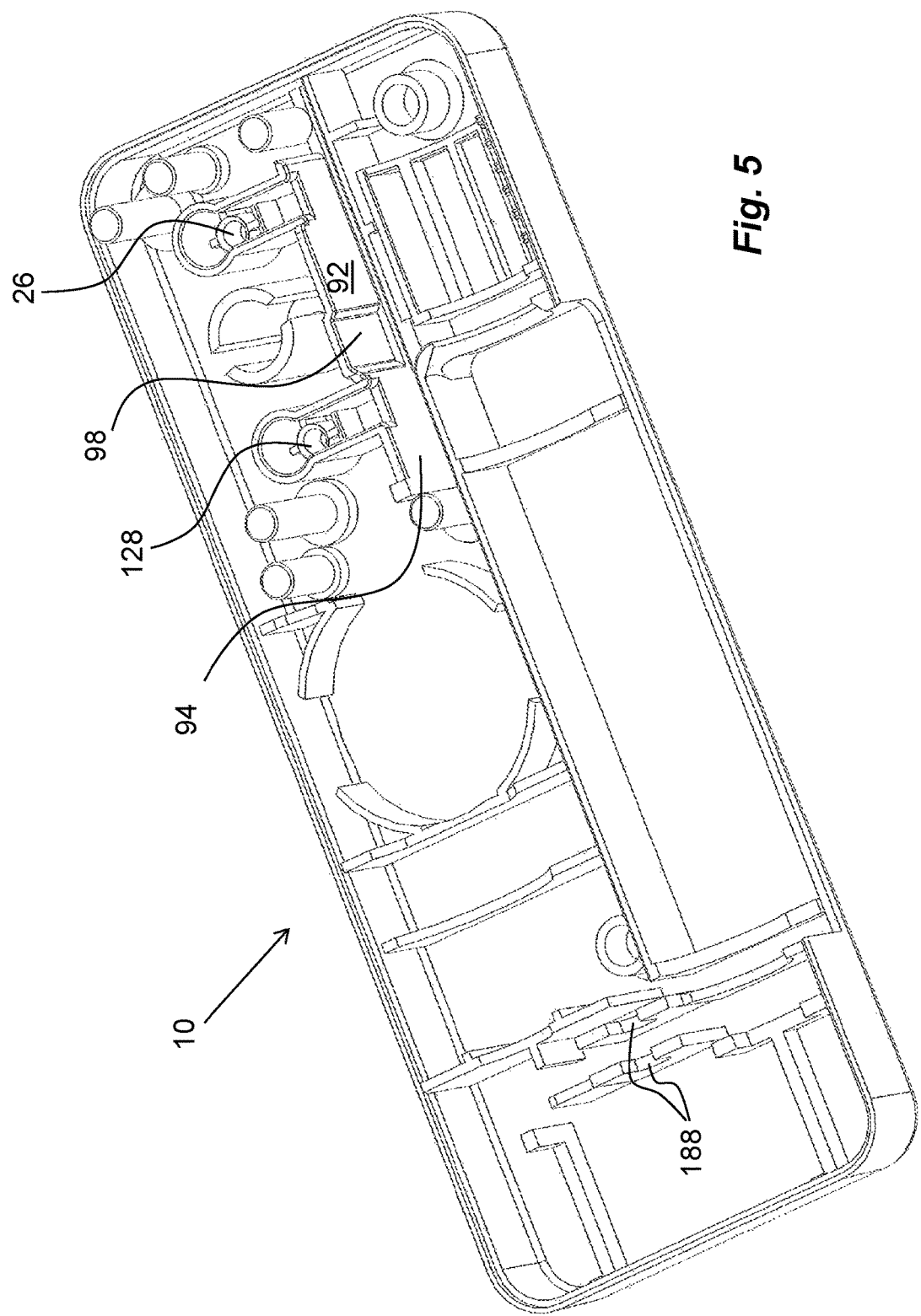
FIG. 5 shows a different detailed view of components comprised in the medicament delivery device of FIG. 1.
Figure 6:
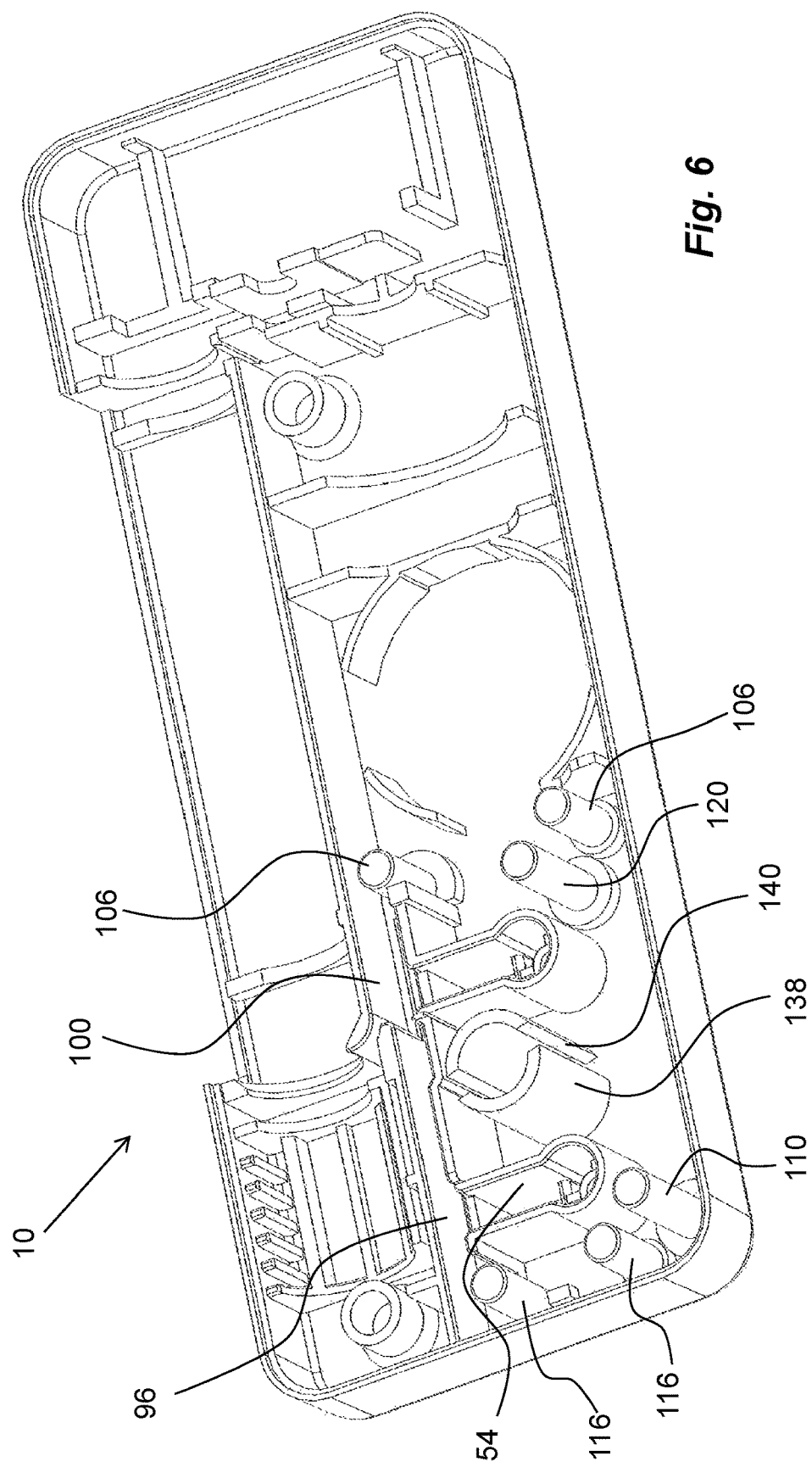
FIG. 6 shows a different detailed view of components comprised in the medicament delivery device of FIG. 1.

The control element 60 is intended to fit into a compartment 92 of the proximal housing part 10, FIG. 5, which compartment 92 is delimited by two parallel wall sections 94, 96, FIGS. 5 and 6, such that the control element 60 is capable of moving or sliding inside the compartment 92 between a first position and a second position, as will be described below. The wall section 94 that is facing the first side surface 58 of the control element 60 is arranged with a recess 98, FIG. 5. The other wall section 96 is arranged with a cut-away portion 100. The function of the recess 98 and the cut-away portion 100 will be described below.

Further, a first thin band-shaped element 102, a penetration ribbon, FIG. 7, is connected to the control element 60 via an first anchoring element 104 attached to one end, which first anchoring element 104 fits into the first seat 78 on the second side surface 76 of the control element 60. The penetration ribbon 102 is guided around two posts 106, fixed on the proximal housing part 10, and the second end of the penetration ribbon 102 is connected to the free end of a first force element in the form of a clock spring 108, hereafter named penetration spring. The penetration spring 108 is wound around a further post 110 fixed in the proximal housing part 10 and with an inner end attached to the post 110.

A second thin band-shaped element 112, a retraction ribbon, is arranged with an second anchoring element 114 attached to an end, which second anchoring element 114 fits into the recess 98 in the wall section 94 of the compartment 92. The retraction ribbon 112 is also guided around two fixed posts 116. A second force element in the form of a clock spring 118, hereafter named retraction spring, is attached to the free end of the retraction ribbon 112. The retraction spring 118 is wound around and attached to, a fixed post 120.

Further, a stop mechanism 121 is arranged in the device for stopping different functions of the device as will be described, see FIG. 2. The stop mechanism 121 comprises a push button 122 is arranged to the device, FIG. 8. It comprises a button with the same design as the start button, i.e. having a central body 124 as well as a shaft 126, FIG. 8, which shaft 126 is intended to fit into a guide post 128 in the proximal housing part 10, FIG. 5. Further, the stop button 122 is operably connected to a support element, a wedge lock pin 130, which is arranged with a protrusion 132 with a similar design as the one for the start button, thus forming a second locking element. The button and the wedge lock pin are further designed as disclosed in connection with the start button, whereby the details of the components will not be described in detail again. The stop button 122 extends through a passage 133 in the distal housing part 12 adjacent the passage 18 of the start button, FIG. 1. The stop button 122 may also be arranged with indicia that provide the user with information regarding its function, such as the word OFF, indicating to a user that this is the button that de-activates the device.

The toothed rack 68 of the control element 60 is in contact with a pinion 134 of a penetration and withdrawal mechanism 135, FIG. 9, placed on an outer surface of a generally tubularly shaped rotator sleeve 136, FIG. 9. The rotator sleeve 136 is journalled on a generally tubular post 138, FIG. 6, in the proximal housing part 10. The tubular post 138 is further arranged with two opposite slits 140 extending along the extension of the post 138. Inside the post 138 a medicament delivery member holder 142, FIG. 9, is arranged so as to be slidable along the extension of the post 138. The medicament delivery member holder 142 has a generally tubular body 144 with a diameter somewhat smaller than the diameter of the post 138. The body 144 is arranged with a wall section 146, and a medicament delivery member 148 is attached centrally in the wall section 146. On the outer surface of the body 144, two oppositely positioned, rectangular, protrusions 150 are arranged. These protrusions 150 have a width that is somewhat smaller than the width of the slits 140 of the post 138 such that the rectangular protrusions 150 can slide along the slits 140 as will be described. At the radially outwardly facing surfaces of the rectangular protrusions 150, two generally cylindrical protrusions 152 are arranged. These cylindrical protrusions 152 are intended to fit into generally spirally extending grooves 154 on an inner surface of the rotator sleeve 136, FIG. 9, the function of which will be described below.

Figure 10A:
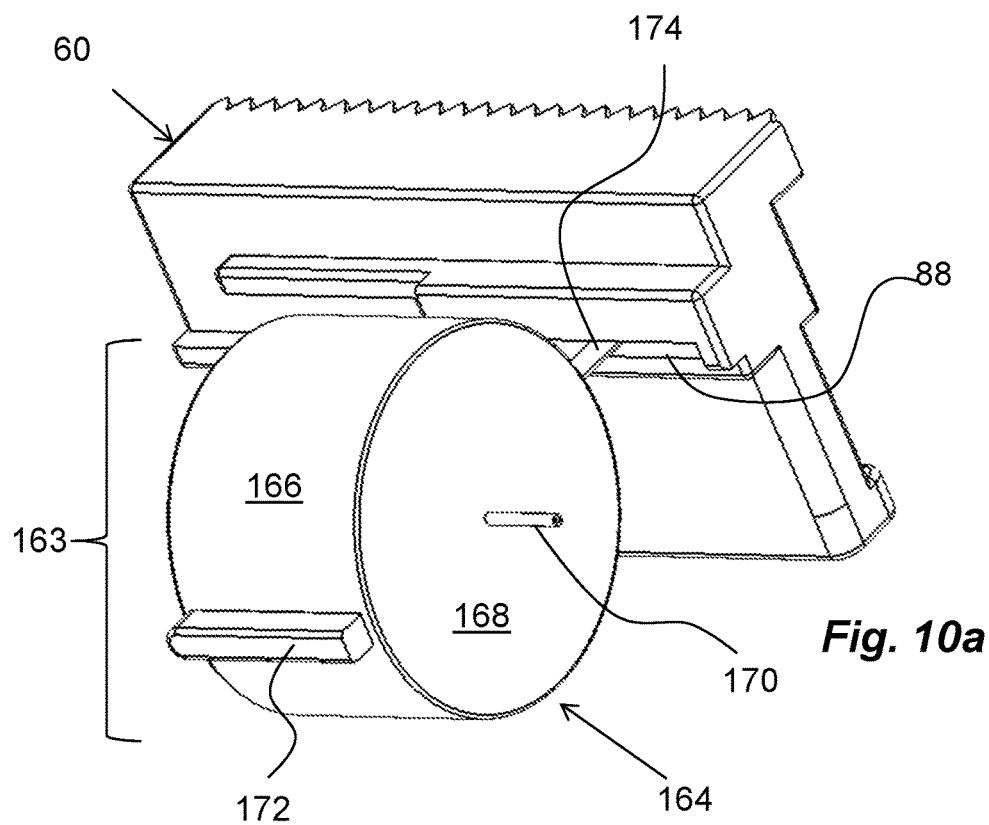
FIG. 10 shows a different detailed view of components comprised in the medicament delivery device of FIG. 1.
Figure 10B:
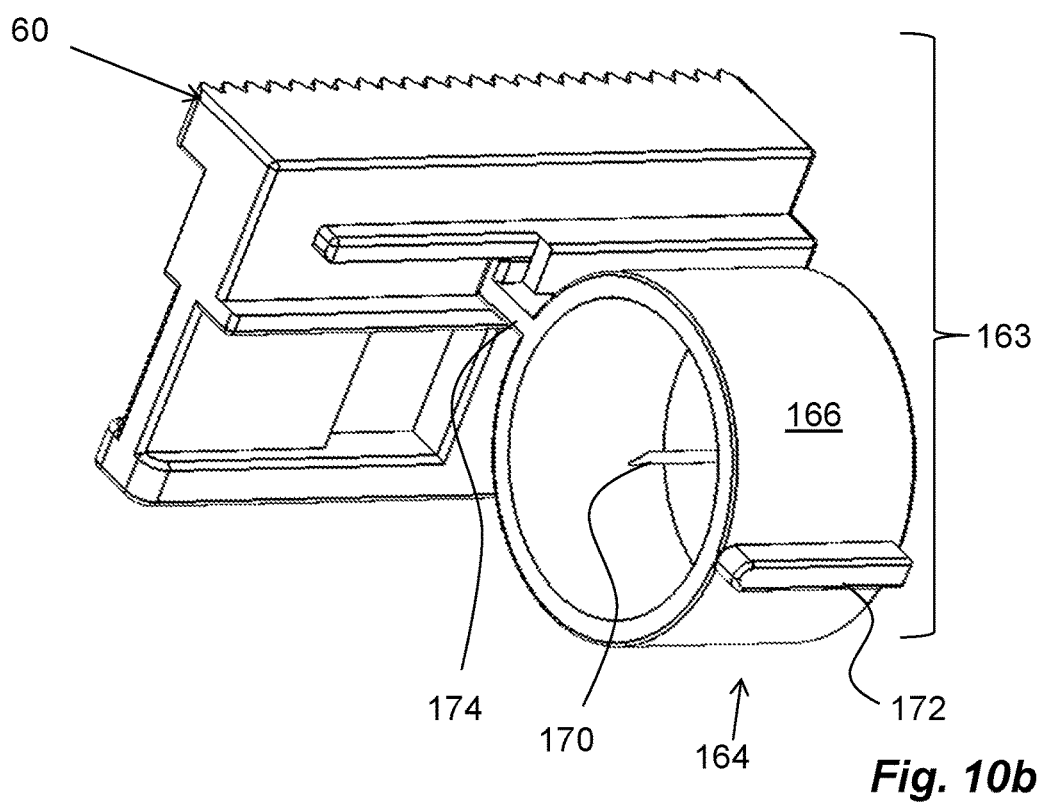
Figure 17:
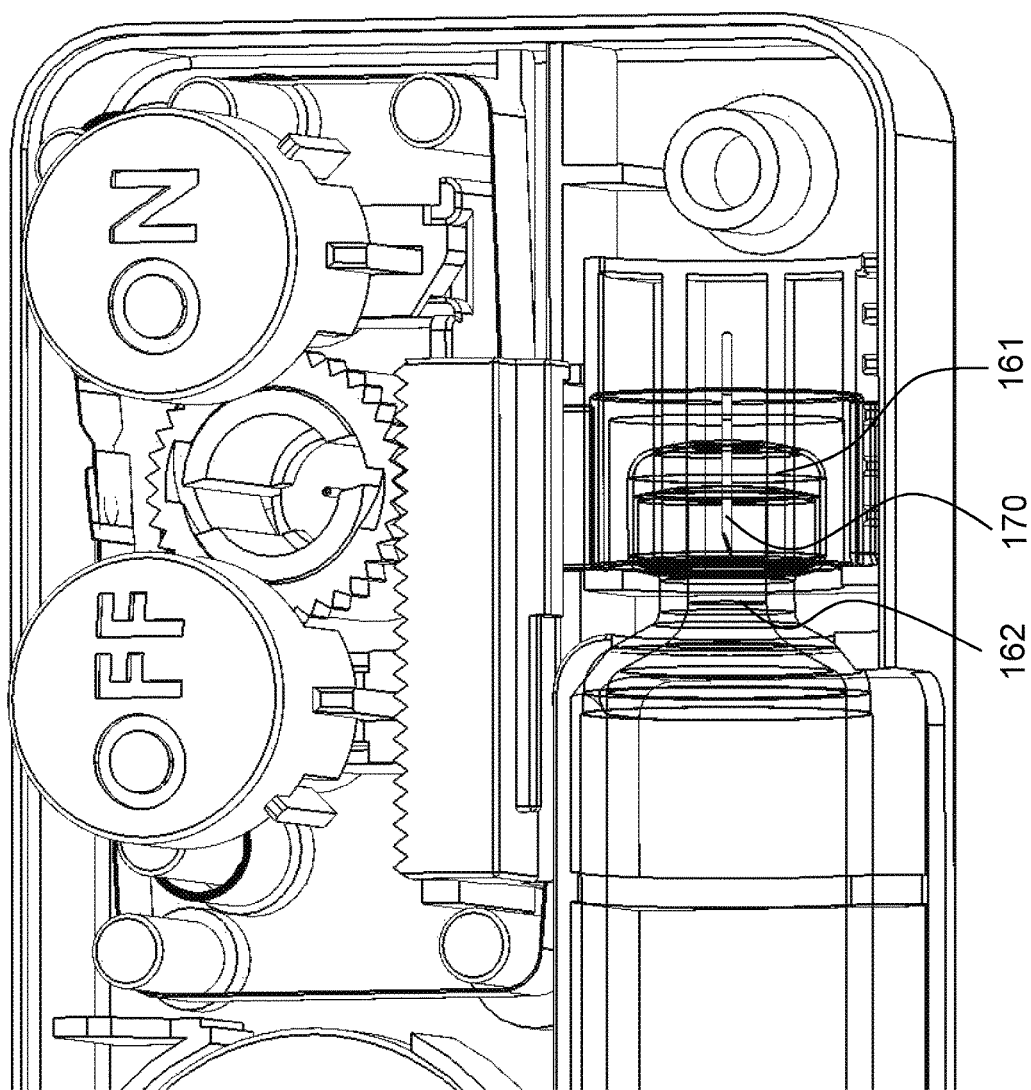
FIG. 17 shows a different functional state of the medicament delivery device of FIG. 1.

The proximal housing part 10 is further arranged to accommodate a medicament container 156. In the preferred embodiment, the medicament container comprises a generally tubular body 158 with a first end arranged with a passage. Inside the passage a generally resilient stopper 160 is arranged, closing the passage, which stopper 160 is movable inside the body 158. The opposite second end of the body is preferably arranged with a neck portion 162, having a central opening. The opening of the neck portion 162 is sealed by a membrane or septum 161 of a pierceable material, FIG. 17. In the vicinity of the neck portion 162 of the medicament container 156, a medicament container connection mechanism 163 is arranged, FIG. 10. The medicament container connection mechanism 163 comprises a piercer 164 that is arranged slidable in the proximal housing part 10, FIGS. 2 and 10. It comprises a generally tubular movable body 166, FIG. 9, having an inner diameter somewhat larger than the diameter of the neck portion 162 of the medicament container 156. The piercer 164 is arranged with a central wall 168. A hollow piercing needle 170 is attached to the centre of the central wall 168. The body 166 is further arranged with two generally radially outwardly extending ledges 172, 174 on opposite sides. One ledge 172 is arranged to be in contact with a fixed support surface on the proximal housing part 10. The other ledge 174 is arranged to fit into the slit 88 of the control element 60, the function of which will be described below.

Figure 11:
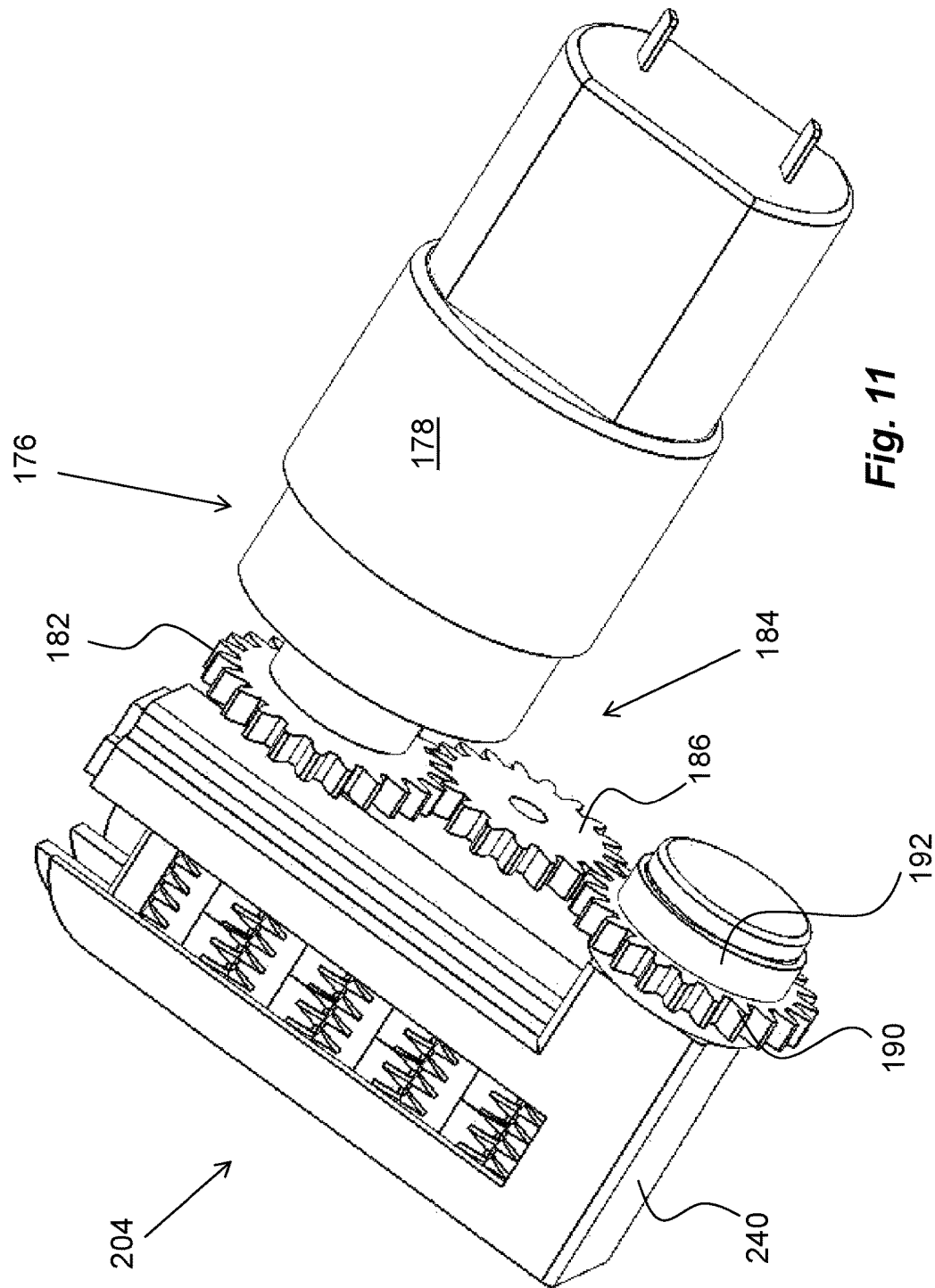
FIG. 11 shows a different detailed view of components comprised in the medicament delivery device of FIG. 1.
Figure 12:
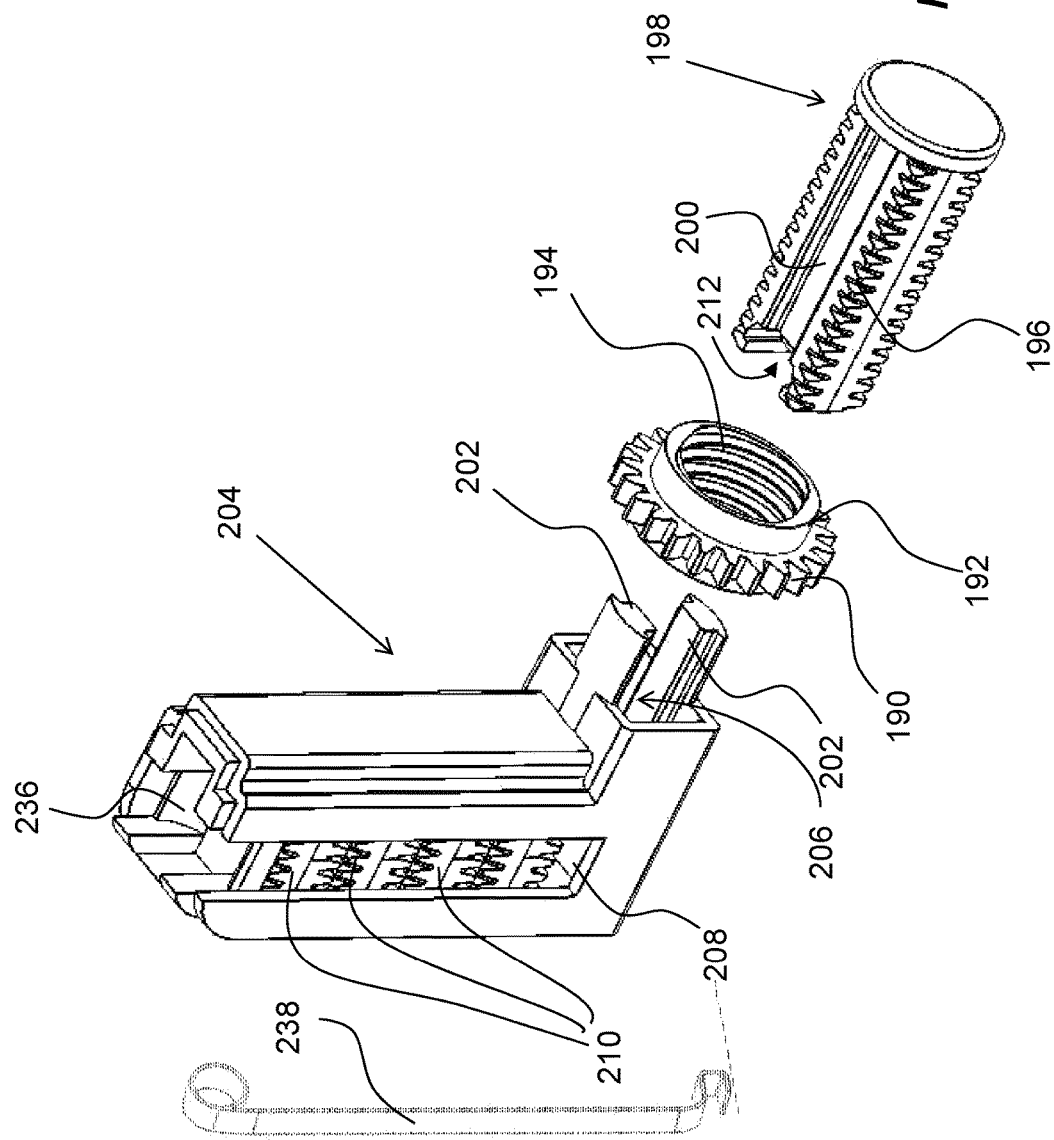
FIG. 12 shows a different detailed view of components comprised in the medicament delivery device of FIG. 1.

The device further comprises a drive unit 176, FIG. 11. The drive unit 176 comprises an electric motor 178 placed inside the housing and held in place by support surfaces of the proximal housing part 10. The electric motor 178 is arranged with a drive shaft 180, FIG. 2. A first cog wheel 182 of a transmission 184 is attached to the drive shaft 180, FIG. 11. The first cog wheel 182 is in engagement with a second cog wheel 186 of the transmission 184, where the second cog wheel 186 is journalled in seats 188 in the first housing part 10, FIG. 5. The second cog wheel 186 is in engagement with circumferentially arranged teeth 190 of a generally ring-shaped plunger rod drive wheel 192. The inner surface of the plunger rod drive wheel 192 is arranged with threads 194, FIG. 12. These threads 194 are in turn arranged to be in engagement with thread segments 196 of a first plunger rod element 198. The first plunger rod element 198 has a generally rectangular shape as seen in a cross-section view, where the thread segments 196 are arranged in the corners of the first plunger rod element 198, as seen in FIG. 12. The proximal end of the first plunger rod element 198 is directed towards the first end of the medicament container 156, wherein the proximal end of the first plunger rod element 198 is intended to be moved in contact with the stopper 160, as will be described below. The dimensions of the first plunger rod element 198 are such that it will fit into the tubular body 158 of the medicament container 156.

The first plunger rod element 198 is arranged with two longitudinally extending grooves 200 on opposite sides thereof. These grooves 200 are intended to cooperate with guide beams 202 arranged extending from a plunger rod element holder 204. The guide beams 202 are arranged on opposite sides of a passage 206 in the plunger rod element holder 204, and the first plunger rod element 198 extends through the passage 206 in an initial position. The guide beams 202 are designed such that they have complementary shapes to, and fit into, the elongated grooves 200 of the first plunger rod element 198. Radially outwardly directed surfaces of the guide beams 202 are designed with a curved shape so as to act as support surfaces for the plunger rod drive wheel 192.

Figure 13:
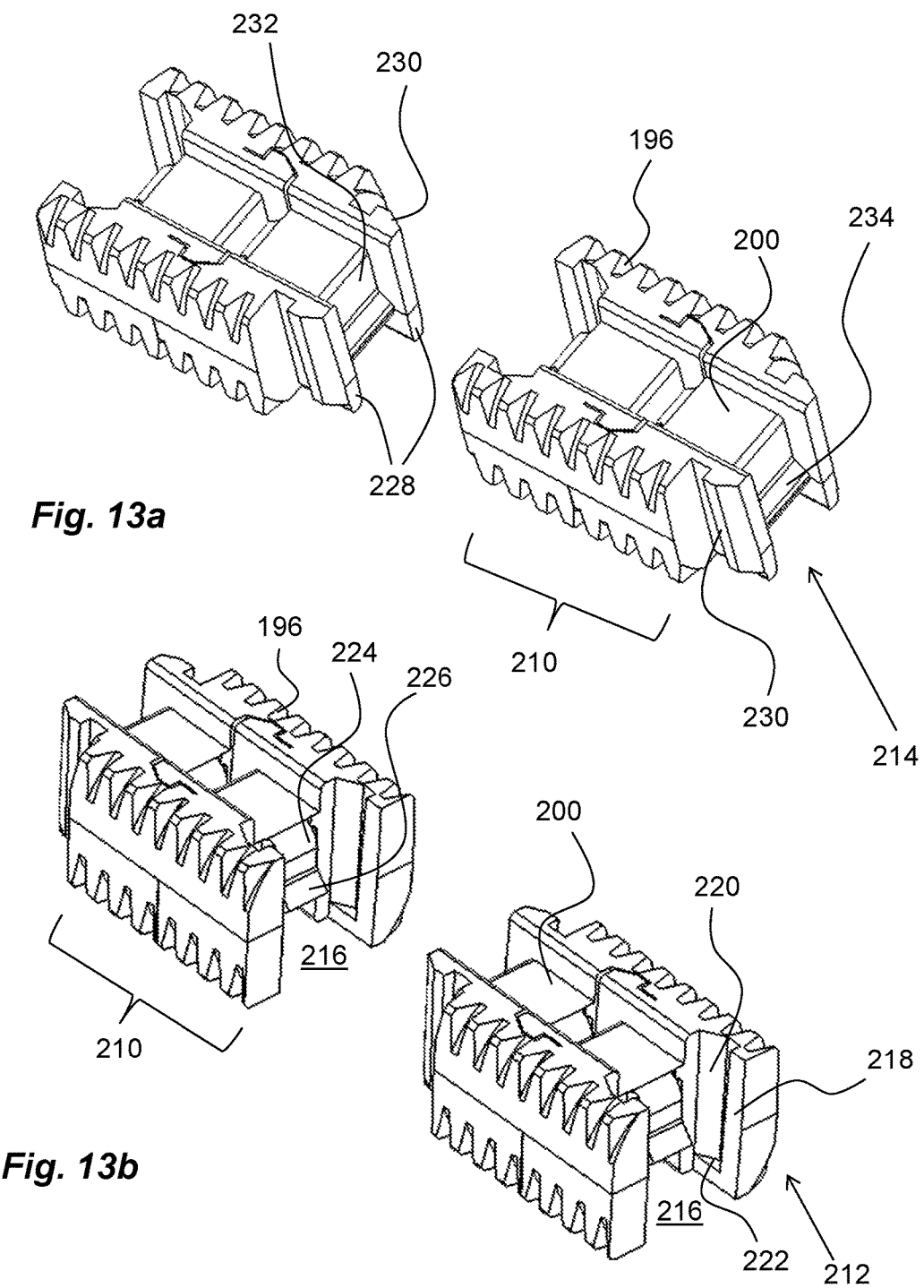
FIG. 13 shows a different detailed view of components comprised in the medicament delivery device of FIG. 1.

The plunger rod element holder 204 is further arranged with a generally rectangularly shaped storage compartment 208, which storage compartment 208 has four side walls and extends generally perpendicularly to the passage 206. In the storage compartment 208, a number of further plunger rod elements 210 are placed. The further plunger rod elements 210 have a shape generally corresponding to the first plunger rod element as seen in FIG. 13, i.e. having a generally rectangular cross-sectional shape, where the corners are provided with thread segments 196, and with longitudinal grooves 200. The further plunger rod elements 210 are arranged with first 212 and second 214 connection elements at their ends, where the first plunger rod element 198 is arranged with a first connection element 212 at its distal end. The first connection element 212 comprises a transversally arranged groove 216. The side edges of the groove 216 are arranged with inwardly directed ledges 218, where the groove 216 and each ledge 218 form a slit 220. Stop surfaces 222 are arranged at a lower end of the slits 220 as seen in FIG. 13. A flexible tongue 224 is arranged in the groove 216, having a certain inclination as well as a wedge-shaped end protrusion 226.

A subsequent plunger rod element 210 that is placed adjacent the first plunger rod element 198 is arranged with a second connection element 214 at its end facing towards the first plunger rod element 198. The second connection element 214 comprises two proximally directed ledges 228, designed with a distance between them, generally corresponding to the width of the groove 216 of the first connection element 212. At the free ends of the ledges 228 outwardly extending protrusions 230 are arranged, which protrusions 230 have a cross-sectional shape complementary to the shape of the slits 220 such that the protrusions 230 can slide into the slits 220 when a subsequent plunger rod element 210 is moved in a direction transversal to the longitudinal direction of the plunger rod elements, as will be described.

Further an end surface 232 of the plunger rod element 210 between the protrusions 230 is arranged with a connection element 234, with which the flexible tongue 224 with its wedge-shaped end protrusion 226 may engage when the plunger rod elements are connected as described. All further plunger rod elements 210 in the storage compartment 208 are arranged with the mentioned first and second connection elements 212, 214 so as to create an elongated plunger rod by the interconnected plunger rod elements. The plunger rod elements in the compartment are urged towards the passage 206 by an end piece 236, FIG. 12, placed at the top of the stack of further plunger rod elements 210 in the storage compartment 208. The end piece 236 is tensioned by a generally flat band spring element 238 with one end seated in the end piece 236 and the opposite end in contact with the bottom 240, FIG. 11, of the plunger rod element holder 204.

Figure 2:
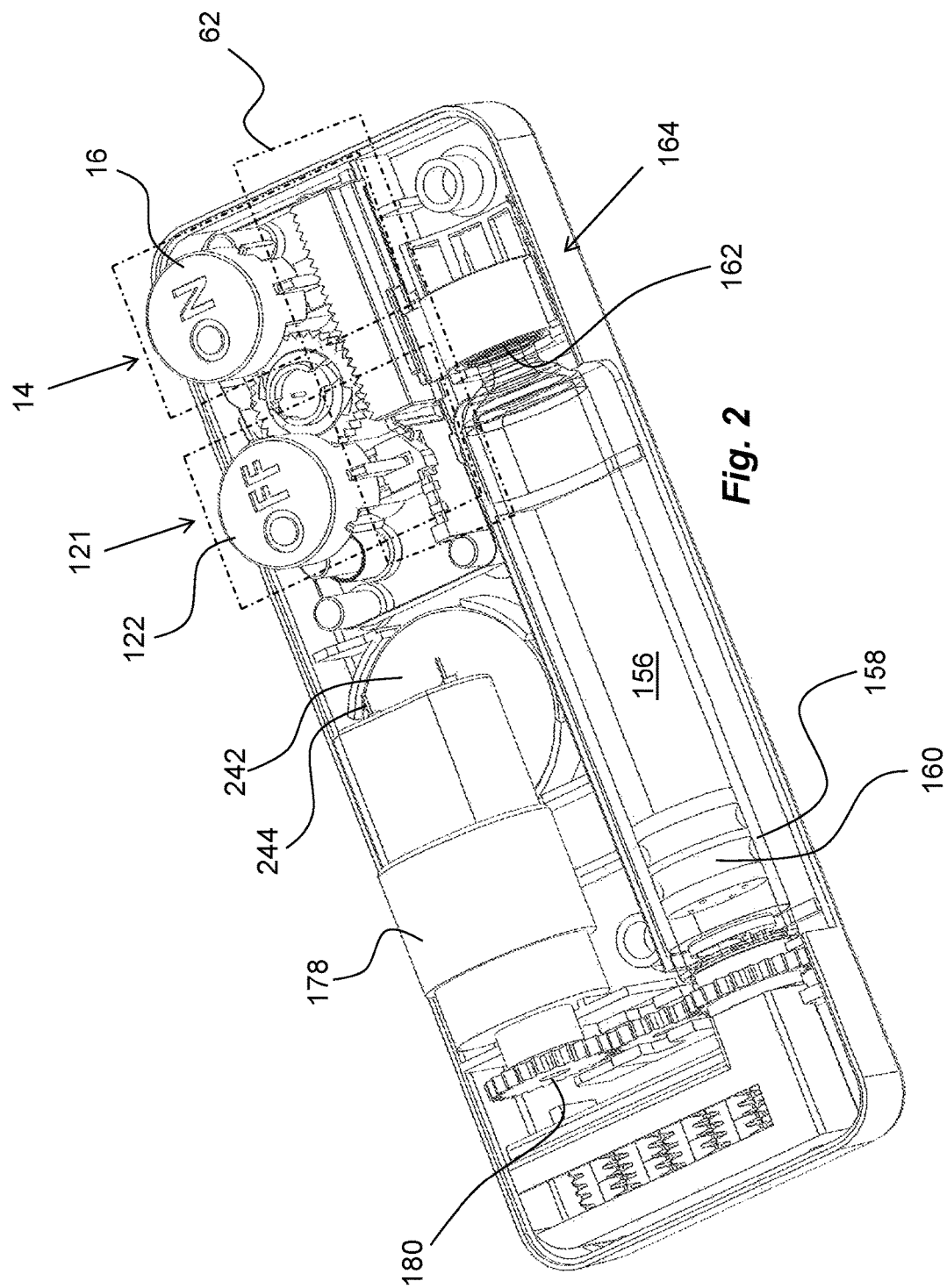
FIG. 2 is another perspective view of the medicament delivery device of FIG. 1 with a housing part removed.
Figure 3:
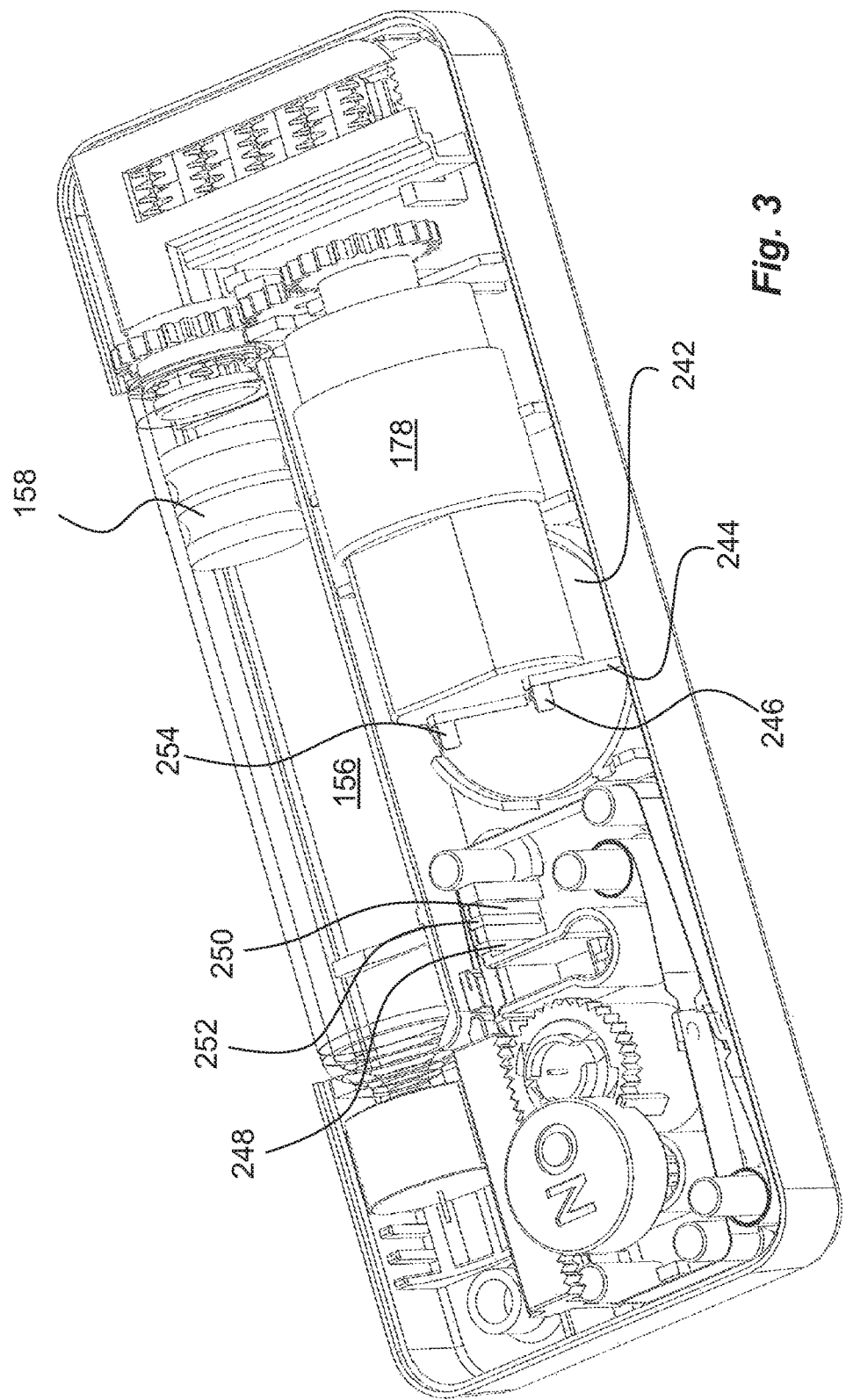
FIG. 3 is a perspective view of the medicament delivery device of FIG. 1 turned 180 degrees in relation to FIG. 2.

The device is further arranged with a suitable power source 242, FIGS. 2 and 3, that in the embodiment shown is a battery of a generally flat and circular shape, a so called button cell. It is however to be understood that other types of power sources are feasible within the scope. The poles of the battery are connected to leads where a first lead 244 is connected to an input connector 246 of the electric motor 178, FIG. 3. A second lead 248 is drawn from the battery to a wall section 250 of the compartment 92 in which the control element 60 can move. The end of the second lead 248 is arranged with a flexible end portion capable of contacting the conductive surface 66 of the control element 60. Further, a third lead 252 is arranged adjacent the second lead 248, where the third lead 252 also is arranged with a flexible end portion capable of contacting the conductive surface 66 of the control element 60. The third lead 252 is then connected to a second input connector 254 of the electric motor. The second and third leads are comprised in the power connection elements as will be described. An electric circuit is thus comprised by the battery, the first, the second and the third leads and the electric motor. The conductive surface 66 serves as a switch of the circuit. When the conductive surface contacts the second and the third leads, the circuit is closed, allowing a current to flow through the circuit to drive the electric motor 178.

Figure 14:
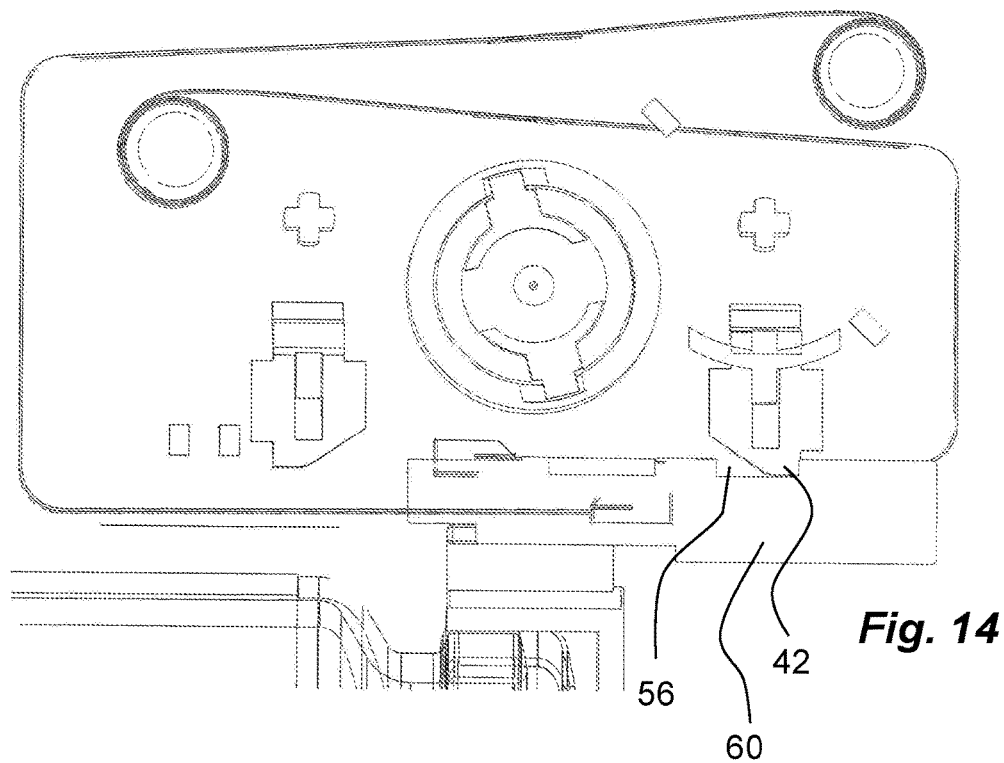
FIG. 14 shows a different functional state of the medicament delivery device of FIG. 1.

The device is intended to function as follows. When delivered to a user, it is energized in that the penetration spring 108 is tensioned and held in that state by the first anchoring element 104 engaged in the first seat 78 of the control element 60, as seen in FIG. 7. The control element 60 in turn is held stationary in the first position against the force of the penetration spring 108 by the protrusion 42 of the wedge-lock pin 40 of the ON-button fitting into the first seat 56, as seen in FIG. 14. The retraction spring 118 is also tensioned and held in that state by its second anchoring element 114 seated in the recess 98 of the compartment 92, as seen in FIG. 7.

When the device is to be used a lid (not shown) on the distal housing part 12 is opened and a medicament container 156 is placed in the interior of the device, after which the lid is closed. The device is then attached to the body of the patient with suitable elements. That could for example be an adhesive on the proximal surface of the proximal housing part 10, elastic straps around the body of the patient, for example.

Figure 15:
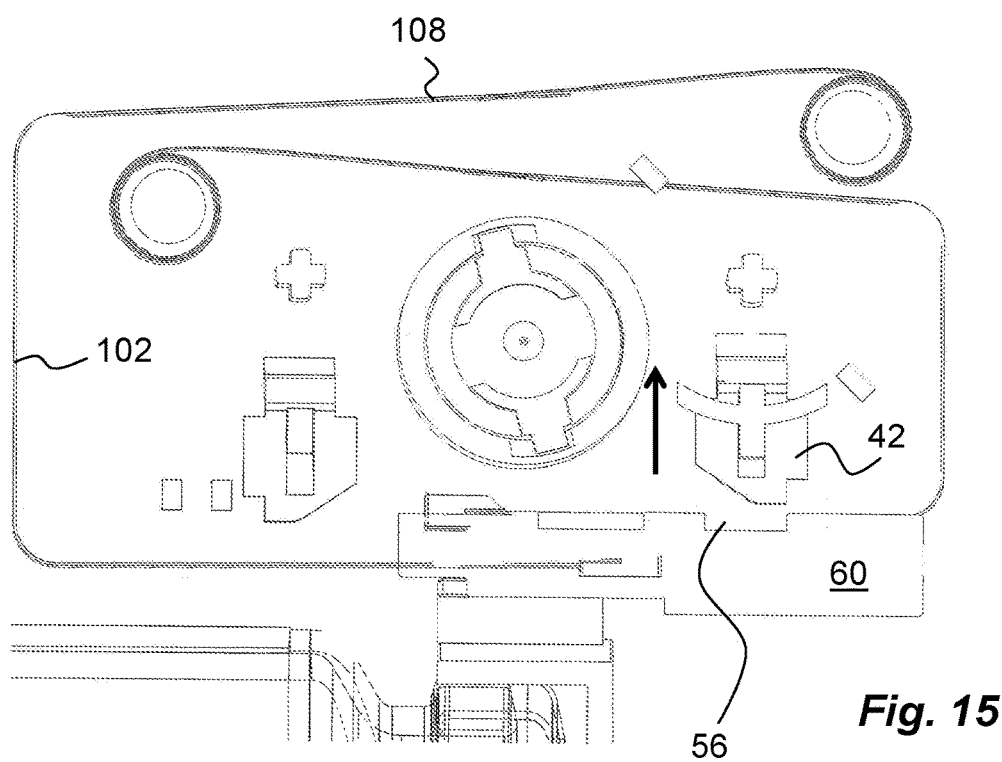
FIG. 15 shows a different functional state of the medicament delivery device of FIG. 1.

When the device is positioned properly, the user may activate it by pressing the on-push button 16 of the activation mechanism 14. The push button 16 will then move in the proximal direction inside the housing whereby the inclined surface 38 of the ledge 36 will act on the wedge lock pin 40 such that its central protrusion 42 is moved out of contact with the first seat 56 of the control element 60, as seen in FIG. 15. The control element 60 is now free to move from the first position and will be pulled towards the second position by the pre-tensioned penetration spring 108 fitting in the first seat 78 of the control element 60. The second anchoring element 114 of the retraction spring 118 is still seated in the recess 98 of the compartment 92 and will slide in the groove 72 of the control element 60 when the latter is moved.

Figure 16:
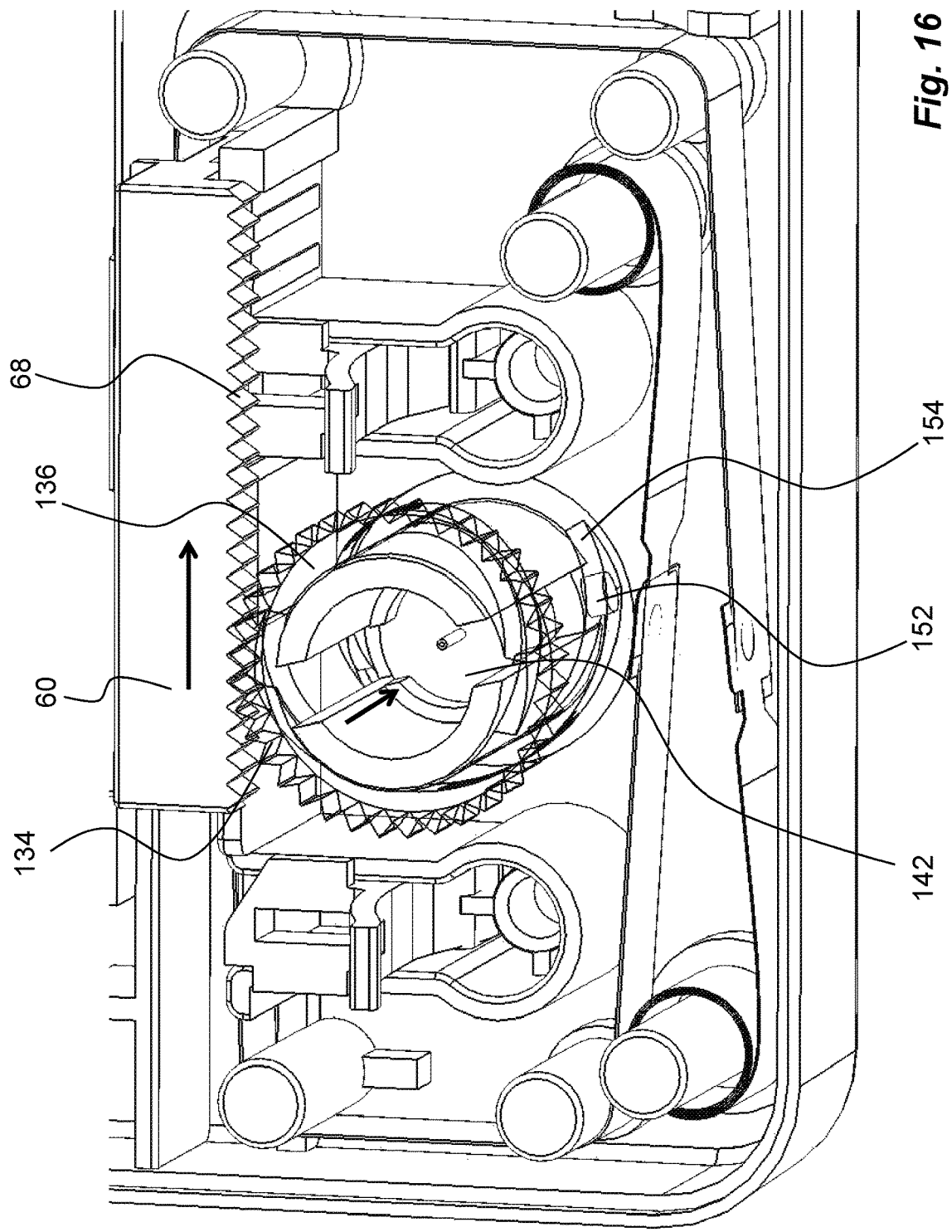
FIG. 16 shows a different functional state of the medicament delivery device of FIG. 1.

As the control element 60 moves, its toothed rack 68 will act on the pinion 134 of the rotator sleeve 136. The rotation of the rotator sleeve 136 will cause the cylindrical protrusions 152 of the medicament delivery member holder 142 to slide in the spiral grooves 154 of the rotator sleeve 136, whereby the medicament delivery member holder 142 will move in the proximal direction and so will the medicament delivery member 148, whereby a penetration is obtained, FIG. 16.

The movement of the control element 60 will cause the second ledge 174 of the piercer 164 to come in contact with the stop surface 90 in the slit 88 of the control element 60. This will cause the piercer 164 to move towards the medicament container 156. The end of the piercing needle 170 will then penetrate the septum 161 of the medicament container, whereby a fluid connection is obtained between the interior of the medicament container 156 and the medicament delivery member 148, FIG. 17, via a flexible tube (not shown).

Figure 18:
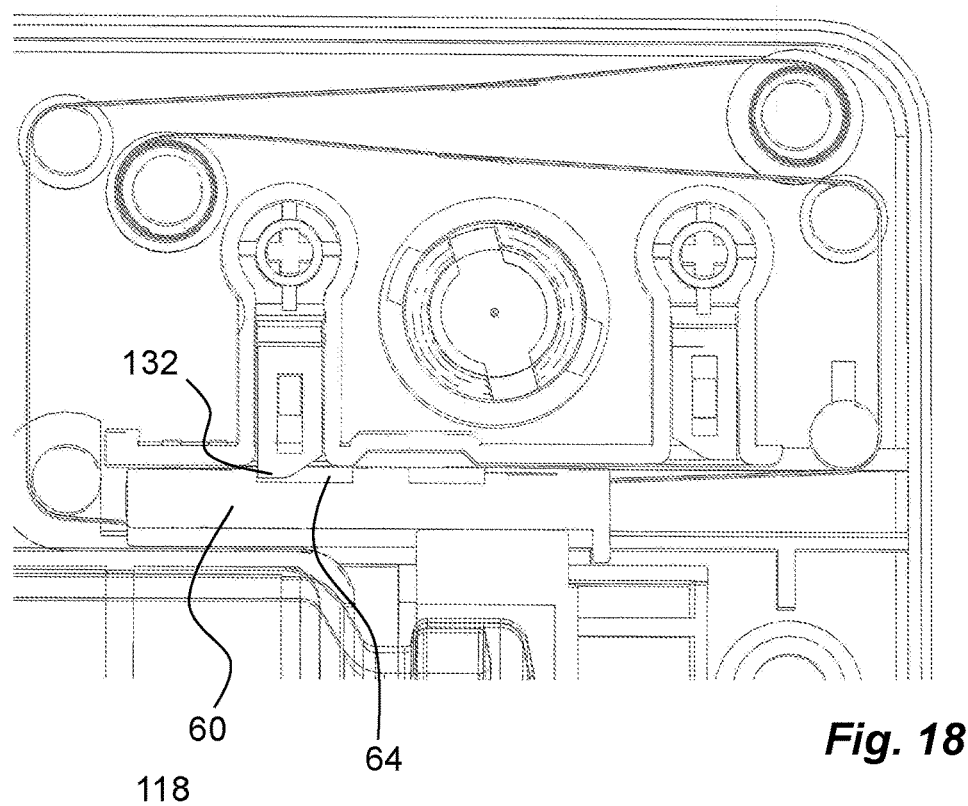
FIG. 18 shows a different functional state of the medicament delivery device of FIG. 1.
Figure 19:
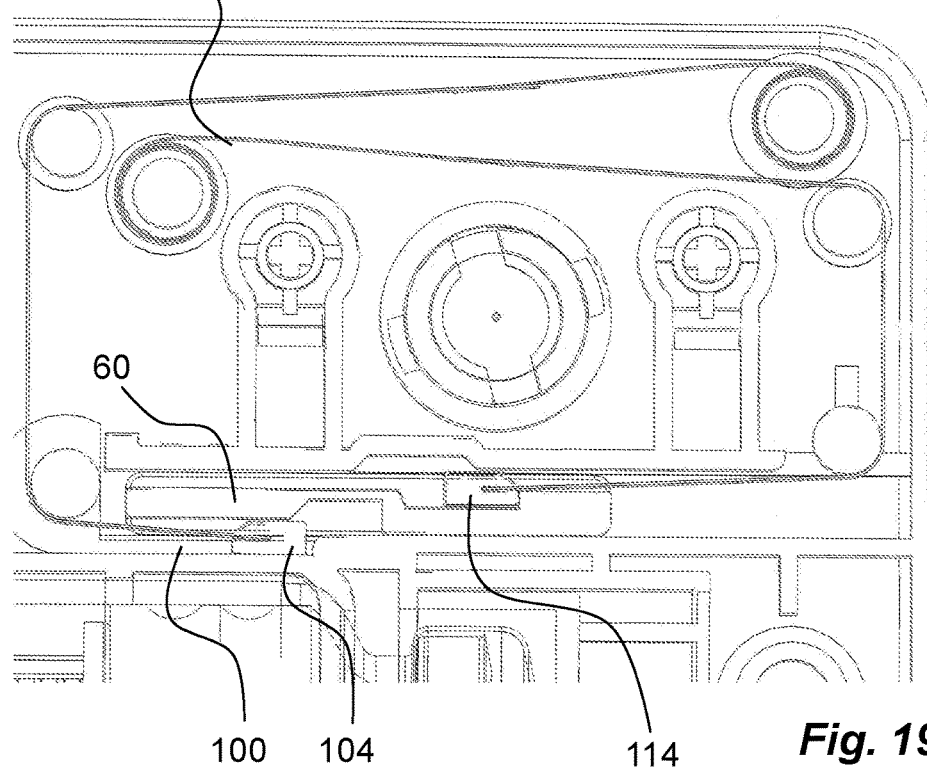
FIG. 19 shows a different functional state of the medicament delivery device of FIG. 1.

Further movement of the control element 60 will cause the conductive area 66 of the control element 60 to be moved into the second position and into contact with the second and the third leads, 248, 252. In this position, the protrusion 132 of the wedge lock pin 130 of the stop button 122 will enter the second seat 64 of the first side surface 58 of the control element 60, FIG. 18, thereby locking the control element 60 in this position. The penetration spring 108 is now released from the control element 60 because its first anchoring element 104 has come to the cut-away portion 100 in the wall of the compartment 92 and the second anchoring element 114 of the retraction spring 118 is released from the recess 98 in the side wall of the compartment 92 because the second anchoring element 114 now can slide into the third seat 70 of the control element 60, as seen in FIG. 19. However, the retraction spring 118 is still tensioned since the control element 60 is held by the second locking element 132.

Further, the contact of the leads 248, 252, with the conductive area 66, i.e. the power connection elements, will cause the power source 242 to be connected to the electric motor 178, thereby energizing the latter to start rotating the first cogwheel 182. The rotation of the first cogwheel 182 is transmitted to the second cogwheel 186 of the transmission 184 and then to the plunger rod drive wheel 192 via its teeth 190. Since the threads 194 of the plunger rod drive wheel 192 is in contact with the thread segments 196 of the first plunger rod element 198, the first plunger rod element 198 is moved in the direction of the medicament container 156. When the proximal end of the first plunger rod element 198 comes in contact with the stopper 160, it will move the stopper 160 inside the medicament container towards its neck portion 162, whereby medicament will be forced through the fluid connection and through the medicament delivery member 148, thereby delivering medicament to the user.

Figure 20:
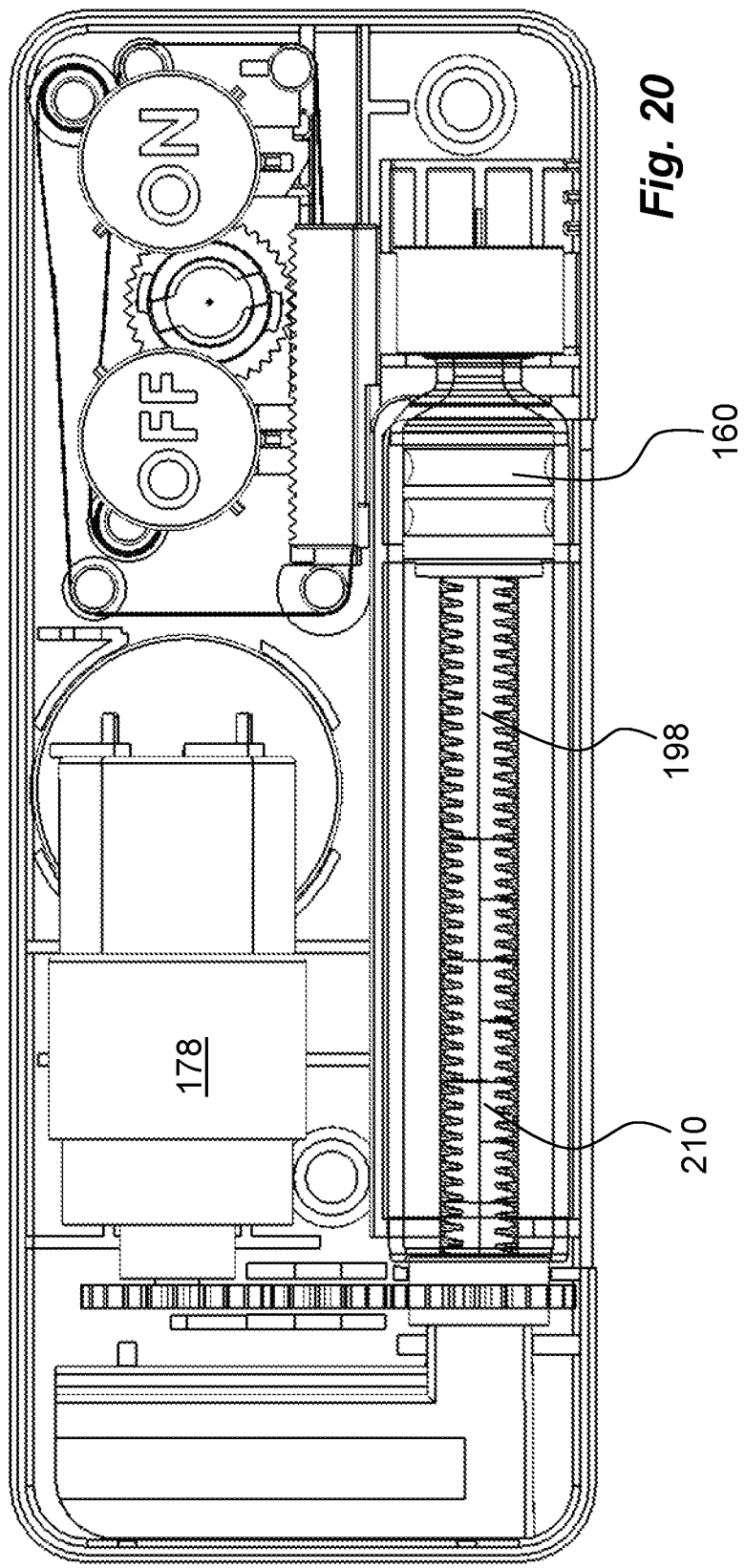
FIG. 20 shows a different functional state of the medicament delivery device of FIG. 1.

When the first plunger rod element 198 has moved a distance towards and inside the medicament container 156, the space behind the first plunger rod element 198 is so large that a subsequent plunger rod element 210 may be pushed in the vertical direction by the flat band spring element 238 acting on the uppermost positioned end piece 236 in the storage compartment 208. When the following plunger rod elements 210 are pushed downwards in the vertical direction, they are connected to a previous plunger rod element in that the ledges 228 of the first connection elements 212 of the subsequent segment fit into the slits 220 of the groove 216 of the second connection element 214 and wherein the plunger rod elements are inter-locked by the flexible tongues 224 engaging the connection elements 234. In this manner a sequential "building" of a continuous plunger rod is performed with the segments while performing injection of medicament from the medicament container 156 through the medicament delivery member 148, as seen in FIG. 20.

Figure 21:
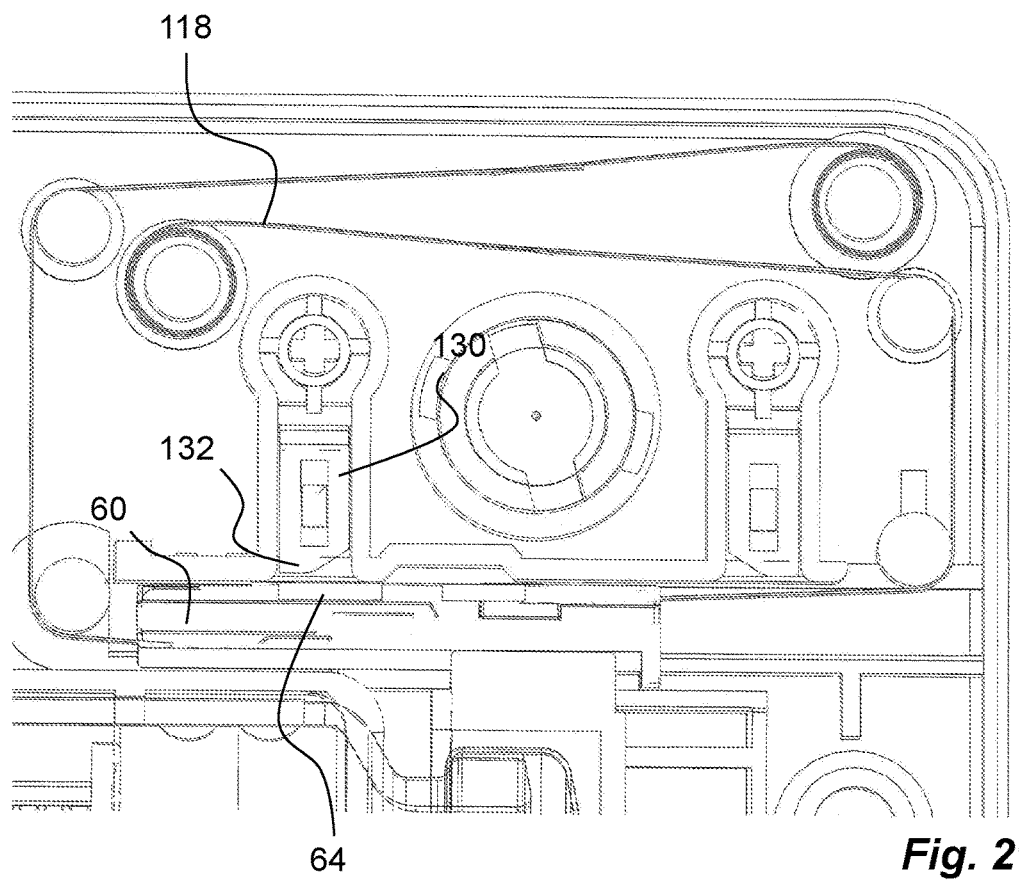
FIG. 21 shows a different functional state of the medicament delivery device of FIG. 1.
Figure 22:
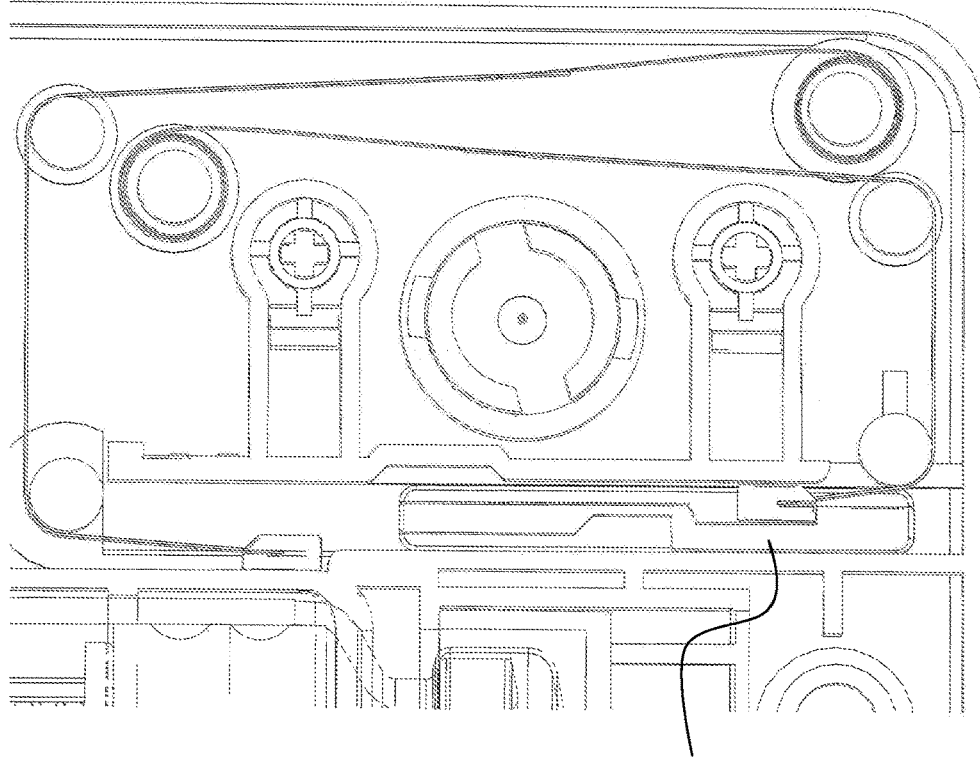
FIG. 22 shows a different functional state of the medicament delivery device of FIG. 1.

When the plunger rod has pushed the stopper 160 inside the medicament container 156 to the most proximal position, whereby the dose delivery sequence is ended, the device can be switched off. In order to do this the OFF-button 122 is depressed. This causes the protrusion 132 of the wedge lock pin 130 of the OFF-button to be moved out of the second seat 64 of the control element 60, thereby releasing the control element, FIG. 21. Due to the force of the retraction spring 118, the control element 60 is now moved back to its original position, i.e. the first position, FIG. 22. The movement of the control element 60 causes the conductive area 66 to be moved away from the leads 248, 252, thereby breaking the electric connection with the power source 242, whereby the electric motor 178 is switched off. Further, the movement of the control element 60 will cause its toothed rack 68 to act on the pinion 134 of the rotator sleeve 136. The rotation of the rotator sleeve 136 in the opposite direction will in turn cause a retraction of the medicament delivery member 148 from its extended position to the initial position where the medicament delivery member is hidden inside the device. The device is now safe to be removed from the body of the user.

If the device is to be used again, the device is opened in a suitable way and the medicament delivery member holder is replaced with a new clean/sterile holder and medicament delivery member. Further the empty medicament container is replaced with a full medicament container.

It is to be understood that the embodiment described above and shown in the drawings is to be regarded only as a non-limiting example of the disclosure and that it may be modified in many ways within the scope of the patent claims.

The invention claimed is:

1. A control mechanism for a medicament delivery device, which medicament delivery device comprises
    a medicament container connection mechanism configured to connect a medicament container with a medicament delivery member;
    a penetration and withdrawal mechanism configured to actuate a penetration and a withdrawal sequence;
    a medicament delivery drive unit configured to expel a medicament from the medicament container;
    an activation mechanism that when activated initiates a penetration and medicament delivery sequence;
    a stop mechanism that when activated initiates a withdrawal sequence;
    wherein the control mechanism further comprises a control member that is configured to move linearly between a first position and a second position, which control member is connectable to the medicament container connection mechanism, to the penetration and withdrawal mechanism, to the medicament delivery drive unit, to the activation mechanism, and to the stop mechanism
    wherein the activation mechanism comprises a manually actuated first locking element and wherein the control member comprises a first seat in which said first locking element is accommodated, such that the control member is connected to the activation mechanism when the control member is in the first position.

2. The control mechanism for a medicament delivery device according to claim 1, wherein the control member is connected to the activation mechanism when the control member is in the first position, wherein the control member is connected to the penetration and withdrawal mechanism and to the medicament container connection mechanism during linear movement of the control member between the first and the second position and wherein the control member is connected to the medicament delivery drive unit and to the stop mechanism when the control member is in the second position.

3. The control mechanism for a medicament delivery device according to claim 1, wherein the control member is further releasably held in the first position by said first locking element against a bias of a pre-tensioned first force element, and wherein manual actuation of the first locking element releases the control member to move linearly from the first position towards the second position under the bias of the first force element.

4. The control mechanism for a medicament delivery device according to claim 3 wherein the first force element comprises a first anchor wherein the first anchor is releasably connected to the first seat, and configured to be disconnected from the first seat when control member arrives at the second position.

5. The control mechanism for a medicament delivery device according to claim 4, wherein the stop mechanism comprises a manually actuated second locking element and wherein the control member comprises a second seat in which said second locking element may be accommodated, and configured such that the control member is connected to the stop mechanism when the control member arrives at the second position.

6. The control mechanism for a medicament delivery device according to claim 5, wherein the control member may further be releasably held in the second position by said second locking element against a bias of a pre-tensioned second force element, and wherein manual actuation of the second locking element releases the control member to move linearly from the first position towards the second position under the bias of the second force element.

7. The control mechanism for a medicament delivery device according to claim 6 wherein the second force element comprises a second anchor and the control member comprises a third seat and wherein the second anchor is configured to be connected to the third seat when the control member arrives at the second position.

8. The control mechanism for a medicament delivery device according to claim 1, wherein the medicament delivery drive unit comprises an electrical circuit having a first flexible end of an electrical lead and a second flexible end of another electrical lead and wherein the control member comprises a conductive surface that connects the first flexible end with the second flexible end when the control member is in the second position such that the electrical circuit is closed.

9. The control mechanism for a medicament delivery device according to claim 1, wherein the penetration and withdrawal mechanism comprises a pinion arranged on a rotatable sleeve, and the control member comprises a toothed rack, and wherein linear movement of the control member between the first position and the second position causes rotation of said rotatable sleeve via interaction between said pinion and said toothed rack.

10. The control mechanism for a medicament delivery device according to claim 1, wherein the medicament container connection mechanism comprises a movable body arranged with a ledge, and the control member comprises a slit, which slit has a stop surface, and wherein linear movement of the control member from the first position to the second position causes movement of the body via interaction between said ledge and said stop surface.

11. A medicament delivery device comprising:
a medicament container connection mechanism configured to connect a medicament container with a medicament delivery member;
a penetration and withdrawal mechanism configured to actuate a penetration and a withdrawal sequence;
a medicament delivery drive unit configured to expel a medicament from the medicament container;
an activation mechanism that when activated initiates, a penetration and medicament delivery sequence;
a stop mechanism that when activated initiates a withdrawal sequence;
a control mechanism for controlling said medicament delivery device,
wherein the control mechanism further comprises a control member that is configured to move linearly between a first position and a second position, which control member is connectable to the medicament container connection mechanism, to the penetration and withdrawal mechanism, to the medicament delivery drive unit, to the activation mechanism, and to the stop mechanism, where the control member further comprises a conductive surface, and
wherein the medicament delivery drive unit comprises an electrical circuit having a first flexible end of an electrical lead and a second flexible end of another electrical lead, where the conductive surface connects the first flexible end with the second flexible end when the control member is in the second position such that the electrical circuit is closed.

12. The medicament delivery device according to claim 11 wherein the medicament container connection mechanism comprises a movable body arranged with a ledge, and the control member comprises a slit, which slit has a stop surface, and wherein linear movement of the control member from the first position to the second position causes movement of the body via interaction between said ledge and said stop surface.

13. The medicament delivery device according to claim 11, wherein the control member is further releasably held in the first position by a first locking element against a bias of a first force element, and wherein manual actuation of the first locking element releases the control member to move linearly from the first position towards the second position under the bias of the first force element,
wherein the first force element comprises a first anchor and the control member comprises a first seat and wherein the first anchor is releasably connected to the first seat, and configured to be disconnected from the first seat when control member arrives at the second position.

14. The medicament delivery device according to claim 13, wherein the stop mechanism comprises a manually actuated second locking element and wherein the control member comprises a second seat in which said second locking element may be accommodated, and configured such that the control member is connected to the stop mechanism when the control member arrives at the second position.

15. The medicament delivery device according to claim 14, wherein the control member may further be releasably held in the second position by said second locking element against a bias of a pre-tensioned second force element, and wherein manual actuation of the second locking element releases the control member to move linearly from the first position towards the second position under the bias of the second force element.

16. A control mechanism for a medicament delivery device, which medicament delivery device comprises
a medicament container connection mechanism configured to connect a medicament container with a medicament delivery member;
a penetration and withdrawal mechanism configured to actuate a penetration and a withdrawal sequence;
a medicament delivery drive unit configured to expel a medicament from the medicament container;
an activation mechanism that when activated initiates a penetration and medicament delivery sequence;
a stop mechanism that when activated initiates a withdrawal sequence;
wherein the control mechanism further comprises a control member that is connected to the activation mechanism when the control member is in a first position, wherein the control member is connected to the penetration and withdrawal mechanism and to the medicament container connection mechanism during linear movement of the control member between the first and a second position and wherein the control member is connected to the medicament delivery drive unit and to the stop mechanism when the control member is in the second position,
wherein the penetration and withdrawal mechanism comprises a pinion arranged on a rotatable sleeve, and the control member comprises a toothed rack, and wherein linear movement of the control member between the first position and the second position causes rotation of said rotatable sleeve via interaction between said pinion and said toothed rack.

17. The control mechanism for a medicament delivery device according to claim 16 where the stop mechanism comprises a manually actuated locking element and wherein the control member comprises a seat in which said locking element may be accommodated, and configured such that the control member is connected to the stop mechanism when the control member arrives at the second position,
wherein the control member may further be releasably held in the second position by said locking element against a bias of a pre-tensioned force element, and wherein manual actuation of the locking element releases the control member to move linearly from the first position towards the second position under the bias of the force element.

18. The control mechanism for a medicament delivery device according to claim 17 wherein the force element comprises an anchor and the control member comprises a second seat and wherein the anchor is configured to be connected to the second seat when the control member arrives at the second position.

* * * * *